(12) United States Patent
Nesvadba et al.

(10) Patent No.: US 6,281,361 B1
(45) Date of Patent: Aug. 28, 2001

(54) DIBENZONAPHTHYRONES

(75) Inventors: Peter Nesvadba, Marly (CH); Joachim Jandke, Steinen (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 09/280,738

(22) Filed: Mar. 29, 1999

(30) Foreign Application Priority Data

Apr. 8, 1998 (CH) .................................................. 838/98
Sep. 11, 1998 (CH) ................................................ 1861/98

(51) Int. Cl.$^7$ ................................................ C07D 311/78
(52) U.S. Cl. .................................... 546/276; 549/264
(58) Field of Search ...................... 549/276, 264

(56) References Cited

U.S. PATENT DOCUMENTS

| 5,072,055 | 12/1991 | Illy et al. | 568/805 |
| 5,614,572 | 3/1997 | Nesvadba et al. | 524/111 |
| 5,626,633 | 5/1997 | Roschger | 8/506 |

FOREIGN PATENT DOCUMENTS 1052017   3/1959   (DE).

OTHER PUBLICATIONS

Becker et al., J. Org. Chem., vol. 47, (1982), pp. 1095–1101.
Ch. Marschalk, Soc. Chim., 5$^e$ Sér., T. 9, pp. 826–832, (1942).
Becker et al., Aust. J. Chem., vol. 38, pp. 97–110, (1985).
Chatterjea et al., Jour. Indian Chem. Soc., vol. 45, no. 1, pp. 35–44, (1968).
Saalfrank et al., Chem. Ber. vol. 117, pp. 666–671, (1984).
Shibata et al., Chemistry Letters, pp. 511–514, (1979).
Kubota et al., Tetrahedron Letters No. 39, pp. 4671–4674, (1966).
Chatterjea, Jour. Indian Chem. Soc., vol. 36, No. 2, pp. 69–75, (1959).
Becker et al., J. Org. Chem., vol. 42, No. 18, pp. 2966–2973, (1977).
Ma et al., J. Org. Chem., vol. 56, pp. 6110–6114, (1991).
Stork et al., Amer. Chem. Soc., vol. 78, pp. 4604–4608, (1956).
Fujisawa et al, J. Org. Chem., vol. 38, No. 4, pp. 687–690, (1973).
Degering et al., J. Amer. Chem. Soc., vol. 74, pp. 3599–3601, (1952).
Kozlikovskii et al., Zh. Org. Khim., vol. 20, No. 1, pp. 121–124, (1984).

*Primary Examiner*—Amelia Owens
(74) *Attorney, Agent, or Firm*—David R. Crichton

(57) ABSTRACT

Dibenzonaphthyrone of formula (I)

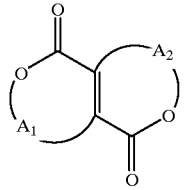

(I)

wherein $A_1$ and $A_2$ independently of each other are unsubstituted or mono- to tetra-substituted o-$C_6$–$C_{18}$arylene, with the proviso that formula (I) does not represent a dibenzonaphthyrone of the formula

II

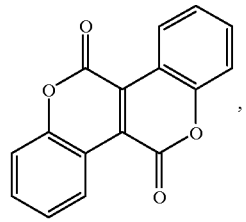

III

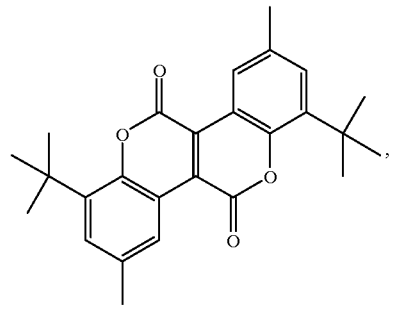

IV

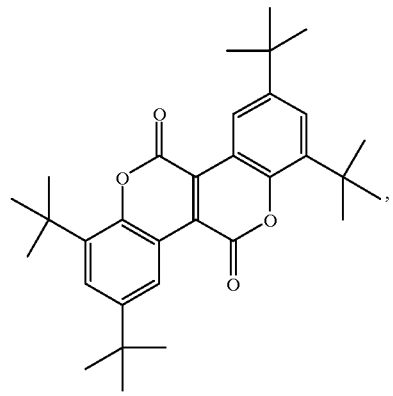

-continued
V
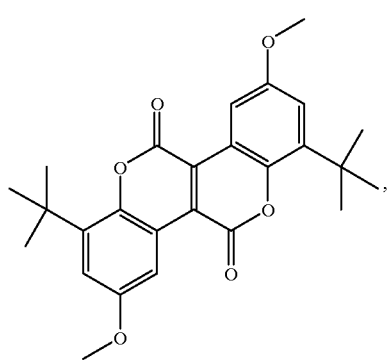
VI
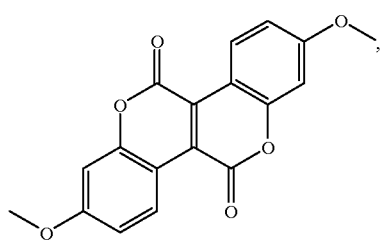
VII
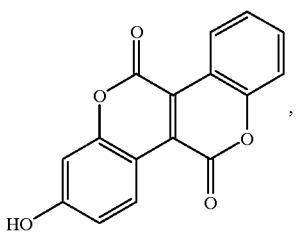
VIII
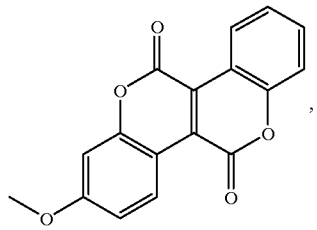
IX
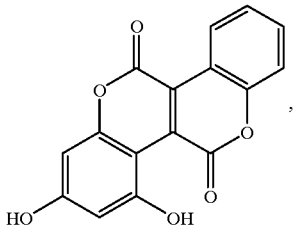
-continued
XI
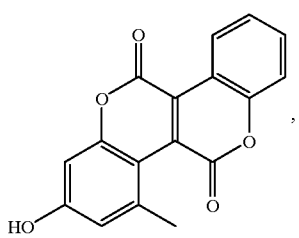
XII
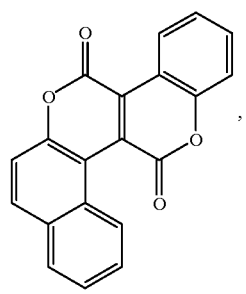
XIII
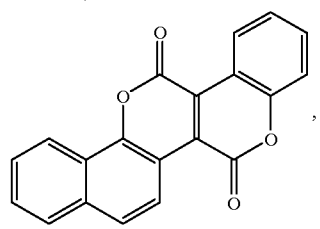
XIV
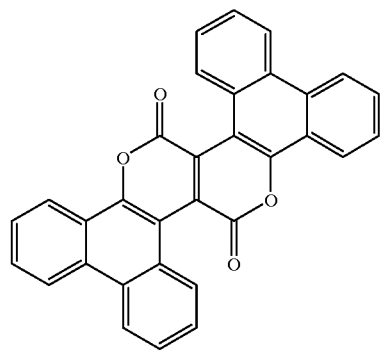
or
XV
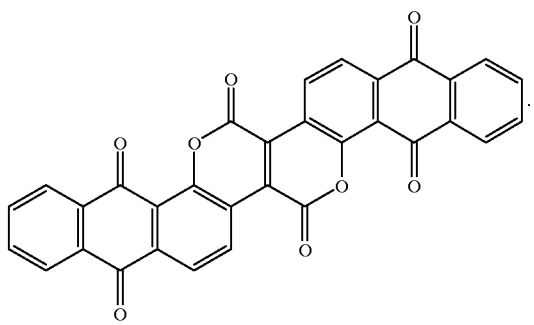
The invention further relates to processes for the preparation thereof, to the use thereof for colouring/pigmenting high-molecular-weight organic material and to substance compositions comprising dibenzonaphthyrones.
3 Claims, No Drawings

DIBENZONAPHTHYRONES

The present invention relates to novel dibenzonaphthyrones, to processes for the preparation thereof, to a process for colouring/pigmenting organic or inorganic, high-molecular-weight or low-molecular-weight material with dibenzonaphthyrones and to substance compositions comprising dibenzonaphthyrones.

Dibenzonaphthyrones of the formula

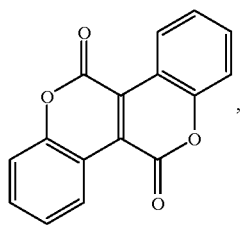
II

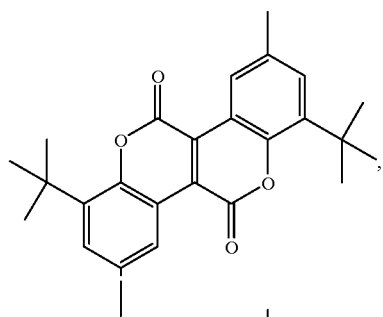
III

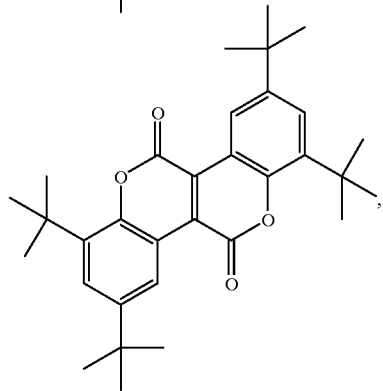
IV

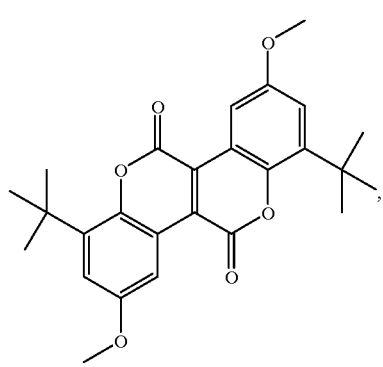
V

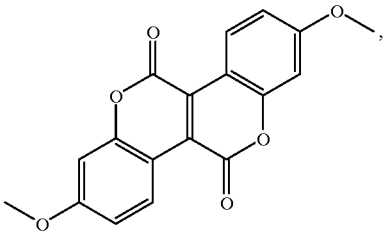
VI

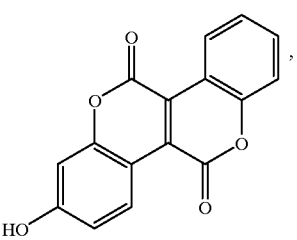
VII

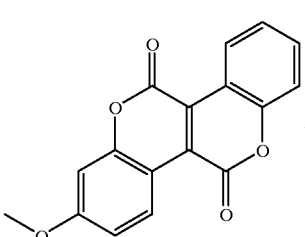
VIII

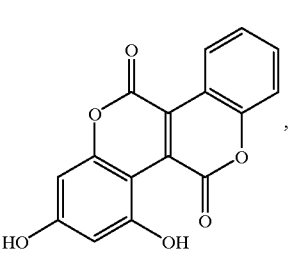
IX

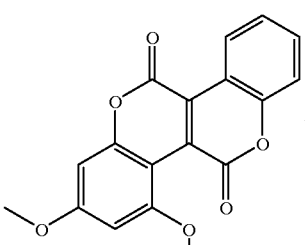
X

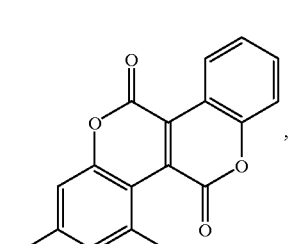
XI

XII
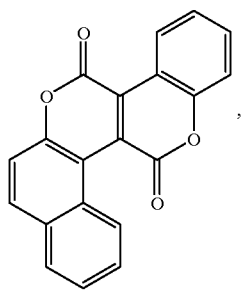,

XIII
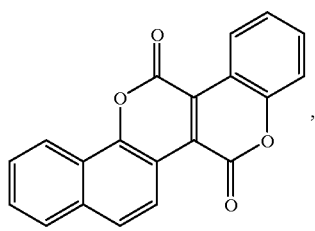,

XIV
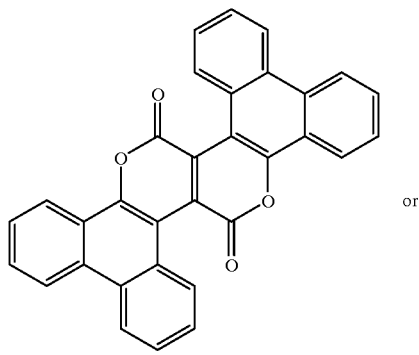 or

XV
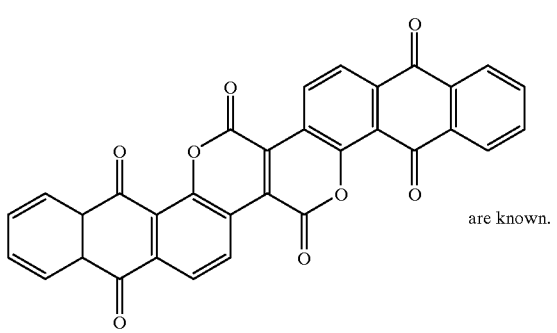

are known.

H. D. Becker et al., Aust. J. Chem., 38(1), 97–110, 1985 describe the compounds of formulae (II) to (V).

Dibenzonaphthyrones of formulae (VI) to (XIII) are known from J. Indian. Chem. Soc., 45, 35 (1968), J. N. Chatterjea et al.

The dibenzonaphthyrone of formula (XIV) is known from Chem. Ber., 117(2), 666–671, 1984, Saalfrank, R. W. et al.

The dibenzonaphthyrone of formula (XV) is known from Bull. Soc. Chim. Fr., $5^e$sér.,T.9, 826 (1942), Ch. Marschalk et al.

The industrial use of dibenzonaphthyrones has been negligible hitherto since their difficult preparation from complicated starting materials is uneconomic and/or the use of oxidising agents containing heavy metals is ecologically unsound.

Aust. J. Chem., 38(1), 97–110, 1985, H. D. Becker et al. disclose, for example, the preparation of dibenzonaphthyrone from isoxindigo, which is difficult to obtain synthetically, by base-catalysed isomerisation, or, Chem. Ber. 117(2), 666–671, Saalfrank, R. W. et al., the isomerisation of coumarin, which has to be prepared in several stages, and, Chem. Lett., 1301–1304, 1979, Shibata K. et al., photo-oxidative multiple-stage preparation from flava-nonol compounds, or J. Indian Chem. Soc. 45, 35–44, 1968, Chatterjea, J. N. et al., condensation from coumarin or trans-2,2dimethoxydicyanostilbene.

Tet. Left., 39, 4671–4674, 1966, Kubota, T. et al. discloses the preparation of dibenzonaphthyrone by oxidation with potassium permanganate and, Bull.Soc.Chim. Fr., $5^e$sér.,T.9, 826 (1942), Ch. Marschalk et al., oxidation with iron chloride or chromic acids.

Fluorescing properties of dibenzonaphthyrones, both in solution and in the crystalline state, are mentioned in Aust. J. Chem., 38(1), 97–110, 1985, H. D. Becker et al.

The use of dibenzonaphthyrones as colourants is not known.

Their difficult preparation makes them too expensive for most purposes.

The problem underlying the invention was therefore to find novel dibenzonaphthyrones that are suitable as colourants or fluorescent agents, especially for colouring/pigmenting organic or inorganic, high-molecular-weight or low-molecular-weight material, but especially high-molecular-weight organic material. In addition, the problem consisted of finding a simpler and cheaper process for the preparation of dibenzonaphthyrones.

The present invention relates to novel dibenzonaphthyrones of the general formula (I)

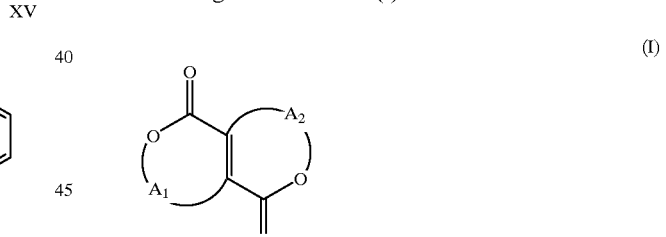

(I)

wherein $A_1$, and $A_2$ are each independently of the other unsubstituted or mono- to tetra-substituted o-$C_6$–$C_{18}$arylene, with the proviso that formula (I) does not represent a dibenzonaphthyrone of the formula

II

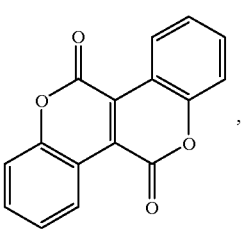,

III
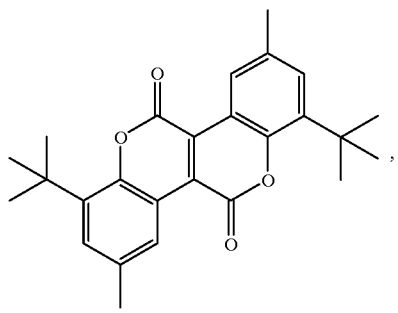
IV
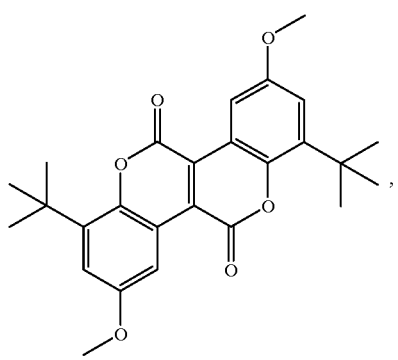
V
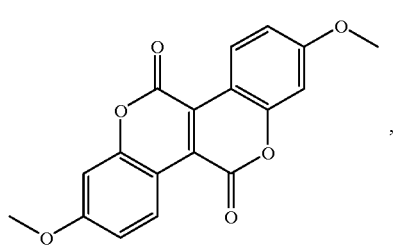
VI
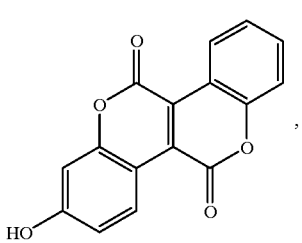
VII
VIII
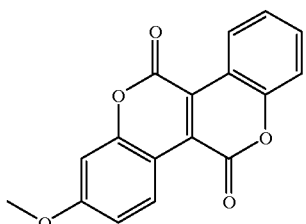
IX
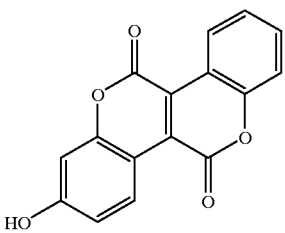
X
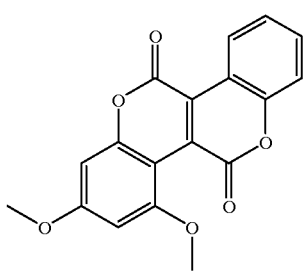
XI
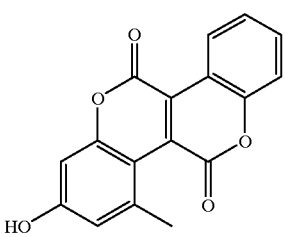
XII
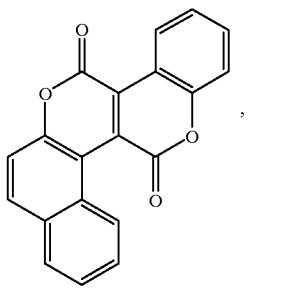
XIII
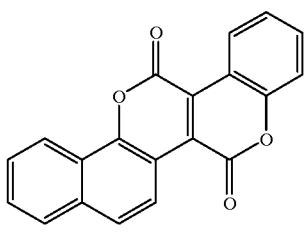

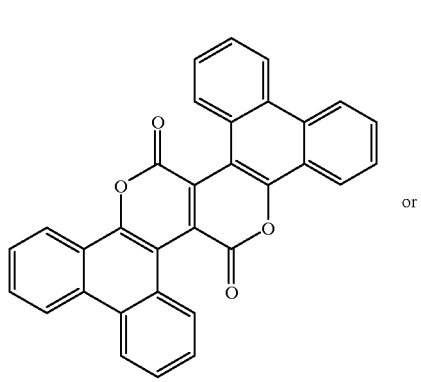

XIV

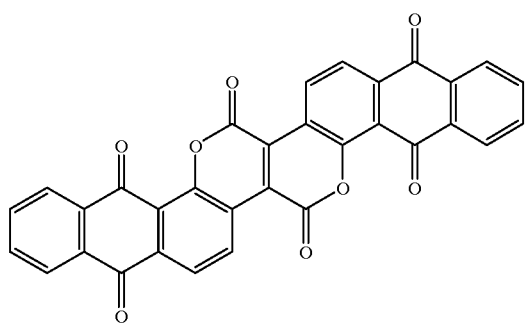

XV o-$C_6$–$C_{18}$Arylene is, for example, 1,2-phenylene, 1,2-naphthylene, 2,3-naphthylene, 1,2-phenanthrylene, 2,3-phenanthrylene, 3,4-phenanthrylene or 9,10-phenanthrylene. If o-$C_6$–$C_{18}$arylene is substituted, the substituents may, independently of one another, be any desired atoms, groups of atoms or radicals, which, depending on their valency, may be bonded to $A_1$ or to $A_2$ by one or more bonds. For example, divalent radicals, such as 1,3-butadien-1,4-ylene or —CH=CH—NH—, may then produce an additional 5- or 6-membered ring fused to $A_1$ and $A_2$, with the proviso that formula (I) does not represent a dibenzonaphtyrone of formulae (II) to (XV).

The compounds of formula (I) are, for example, symmetric or asymmetric dibenzonaphthyrones. If o-$C_6$–$C_{18}$arylene is substituted, the substituent may, for example, be a bridge to a further dibenzonaphthyrone. In that bis-dibenzonaphthyrone structure, two dibenzonaphthyrones may be linked to each other, for example, by an alkylene or cycloalkylene bridge.

Preference is given to the use of dibenzonaphthyrone of the formula

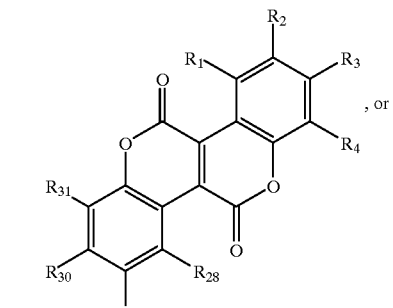

bis-dibenzonaphthyrone of the formula

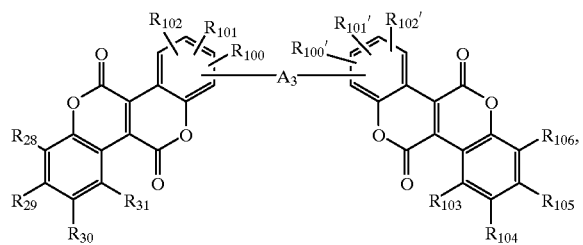

wherein $A_3$ is a single bond, or $C_1$–$C_{24}$alkylene unsubstituted or mono- or poly-substituted by halogen, hydroxy, oxo, cyano, $OCOR_6$, $COOR_6$, $COO^-X^{30}$, $SO_3^-X^+$ or by $SO_3R_6$, a polycyclic radical or $C_5$–$C_{12}$cycloalkylene, each of which may be uninterrupted or interrupted one or more times by O, N, P, S or by $NR_6$, and $C_6$–$C_{24}$arylen and $A_1$–$A_{24}$heteroarylen, and $R_{100}$, $R_{101}$, $R_{102}$ and $R_{100'}$, $R_{101'}$, $R_{102'}$ and $R_{103}$, $R_{104}$, $R_{105}$, $R_{106}$ have independently of one another the same meanings as $R_1$, and $R_1$, $R_2$, $R_3$, $R_4$ and $R_{28}$, $R_{29}$, $R_{30}$ or $R_{31}$ are each independently of the others cyano, $NO_2$, $R_5$, $NR_5R_6$, $NR_7COR_5$, $NR_7COOR_5$, $N=CR_5R_6$, $CONR_7R_8$, $OR_5$, $COOR_5$, $COO^-X^+$, $SR_5$, $SOR_5$, $SO_2R_5$, $SO_2NR_7R_8$, $SO_3R_5$ or $SO_3^-X^+$, it being possible, where applicable, for the pairs of radicals $R_1$ and $R_2$, $R_2$ and $R_3$, $R_3$ and $R_4$ or $R_5$ and $R_6$, and also $R_{28}$ and $R_{29}$, $R_{29}$ and $R_{30}$ or $R_{30}$ and $R_{31}$ to be, in addition, joined together by a direct bond (with the removal of a hydrogen atom at each of the two atoms joined by the bond), so that a 5- or 6-membered ring is produced;

$R_5$ is hydrogen, or $C_1$–$C_{25}$alkyl, $C_5$–$C_{12}$cycloalkyl or $C_2$–$C_{24}$alkenyl each of which is unsubstituted or mono- or poly-substituted by halogen, hydroxy, oxo, cyano, $OCOR_6$, $COOR_6$ or by $COO^-X^+$ and each of which may be uninterrupted or interrupted one or more times by O, S or by $NR_6$, or is $C_6$–$C_{18}$aryl, $C_7$–$C_{18}$aralkyl or $A_5$–$A_{18}$heteroaryl each of which is unsubstituted or mono- or poly-substituted by halogen, nitro, cyano, $OR_6$, $SR_6$, $NR_7R_8$, $CONR_7R_8$, $OCOR_6$, $COOR_6$, $COO^-X^+$, $SO_2R_6$, $SO_2NR_7R_8$, $SO_3R_6$, $SO_3^-X^+$, $NR_7COR_6$ or by $NR_7COOR_6$, $R_6$ is hydrogen, or $C_1$–$C_{25}$alkyl unsubstituted or mono- or poly-substituted by halogen, hydroxy, oxo or by cyano, or OCO—$R_{10}$, COO—$R_{10}$ or COO$^-$X$^+$, or $C_2$–$C_{24}$alkenyl, each of which may be uninterrupted or interrupted one or more times by O, S or NR$_7$, or is $C_6$–$C_{18}$aryl, $C_7$–$C_{18}$aralkyl or $A_5$–$A_{18}$heteroaryl each of which is unsubstituted or mono- or poly-substituted by halogen, nitro, cyano, hydroxy, OR$_7$, SR$_7$, NR$_7$R$_8$, CONR$_7$R$_8$, COOR$_7$, OCOR$_7$, COOH or by COO$^-$X$^+$, $R_7$ and $R_8$ independently of each other are hydrogen, $C_6$–$C_{18}$aryl, $C_7$–$C_{18}$aralkyl, or are $C_1$–$C_{25}$alkyl or $C_2$–$C_{24}$alkenyl each unsubstituted or mono- or poly-substituted by halogen, hydroxy, $C_1$–$C_{12}$alkoxy, OCO—$R_{10}$, COO—$R_{10}$ or by COO$^-$X$^+$, or $R_7$ and $R_8$ together with the common N are pyrrolidine, piperidine, piperazine or morpholine each unsubstituted or mono- to tetra-substituted by $C_1$–$C_4$alkyl, or are carbazole, phenoxazine or phenothiazine, X$^+$ is a cation Li$^+$, Na$^+$, K$^+$, Mg$^{++}_{1/2}$, Ca$^{++}_{1/2}$, Sr$^{++}_{1/2}$, Ba$^{++}_{1/2}$, Cu$^+$, Cu$^{++}_{1/2}$, Zn$^{++}_{1/2}$, Al$^{+++}_{1/3}$ or [NR$_7$R$_8$R$_{10}$R$_{11}$]$^+$, and $R_{10}$ and $R_{11}$ independently of each other are hydrogen, $C_1$–$C_{25}$alkyl, $C_6$–$C_{18}$aryl or $C_7$–$C_{18}$-aralkyl, with the proviso that, in formula (XVIa), dibenzonaphthyrones of formulae (II) to (XV) are excluded.

If a group is poly-substituted, different substituents may be combined.

The present invention further relates to a process for the preparation of dibenzonaphthyrones, which is described in detail hereinafter.

The invention also relates to substance compositions comprising at least one dibenzonaphthyrone selected from the group of compounds of formulae (I) to (XV) and organic or inorganic, high-molecular-weight or low-molecular-weight material, especially high-molecular-weight organic material.

The present invention furthermore relates to a process for colouring/pigmenting organic or inorganic, high-molecular-weight or low-molecular-weight material, especially high-molecular-weight organic material, with at least one dibenzonaphthyrone selected from the group of compounds of formulae (I) to (XV).

Alkyl, alkenyl or alkylene may be straight-chain, branched, monocyclic or polycyclic. Preference is given to $C_1$–$C_{24}$alkyl, $C_2$–$C_{12}$alkenyl and $C_2$–$C_{24}$alkylene. $C_1$–$C_{25}$Alkyl is therefore, for example, most preferably $C_1$–$C_4$alkyl, such as methyl, ethyl, n-propyl, isopropyl, n-butyl, sec-butyl, isobutyl, tert-butyl, cyclobutyl, more preferably $C_1$–$C_6$alkyl, which corresponds to the meanings given for $C_1$–$C_4$alkyl and is, in addition, n-pentyl, 2-pentyl, 3-pentyl, 2,2'-dimethylpropyl, cyclopentyl, cyclohexyl, n-hexyl, and preferably $C_1$–$C_8$alkyl, which corresponds to the meanings given for $C_1$–$C_6$alkyl and is, in addition, n-octyl, 1,1',3,3'-tetramethylbutyl, 2-ethylhexyl, and especially $C_1$–$C_{12}$alkyl, which corresponds to the meanings given for $C_1$–$C_8$alkyl and is, in addition, trimethylcyclohexyl, decyl, menthyl, thujyl, bornyl, 1-adamantyl, 2-adamantyl or dodecyl, and also $C_1$–$C_{15}$alkyl, which corresponds to the meanings given for $C_1$–$C_{12}$alkyl and is, in addition, pentadecyl or tetradecyl, and furthermore hexadecyl, heptadecyl, octadecyl, eicosyl, heneicosyl, docosyl, tetracosyl or pentacosyl.

$C_1$–$C_{24}$Alkylene is therefore, for example, methylene, ethylene, n-propylene, isopropylene, n-butylene, sec-butylene, isobutylene, tert-butylene, cyclobutylene, n-pentylene, 2-pentylene, 3-pentylene, 2,2'-dimethylpropylene, cyclopentylene, cyclohexylene, n-hexylene, n-octylene, 1,1',3,3'-tetramethylbutylene, 2-ethylhexylene, nonylene, trimethylcyclohexylene, decylene, menthylene, thujylene, bornylene, 1-adamantylene, 2-adamantylene, dodecylene, tetradecylene, hexadecylene, heptadecylene, octadecylene, eicosylene, heneicosylene, docosylene or tetracosylene, it being especially $C_1$–$C_{12}$alkylene, and preferably $C_1$–$C_8$-alkylene, more preferably $C_1$–$C_6$alkylene and most preferably $C_1$–$C_4$alkylene. The person skilled in the art will be able to infer the specific meaning of the preferences for the alkylene groups without any difficulty from those given for the alkyl groups.

$C_2$–$C_{12}$Alkenyl is $C_2$–$C_{12}$alkyl that is mono- or poly-unsaturated, it being possible, where applicable, for two or more double bonds to be isolated or conjugated, for example vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 2,5-hexadien-2-yl, 1-p-menthen-8-yl, 4(10)-thujen-10-yl, 2-norbornen-1-yl, 2,5-norbornadien-1-yl, 7,7-dimethyl-2,4-norcaradien-3-yl or the various isomers of hexenyl, octenyl, nonenyl, decenyl or dodecenyl.

$C_1$–$C_{12}$Alkoxy is O—$C_1$–$C_{12}$alkyl, preferably O—$C_1$–$C_4$alkyl.

$C_1$–$C_{12}$Alkyl interrupted by O is, for example, $C_4$alkyl, such as especially —CH$_2$—CH$_2$—O—CH$_2$—CH$_3$. $C_1$–$C_{12}$Alkyl interrupted twice by O is, for example, $C_6$alkyl, such as especially —CH$_2$—CH$_2$—O—CH$_2$—CH$_2$—O—CH$_2$—CH$_3$. $C_1$–$C_{12}$Alkyl substituted by oxo is, for example, $C_2$alkyl, such as especially —C(=O)—CH$_3$.

$C_1$–$C_{12}$Alkyl substituted by oxo and interrupted by O is, for example, $C_8$alkyl substituted by oxo and interrupted by O, such as especially —(CH$_2$)$_3$—O—C(=O)—C(CH$_3$)$_3$, —C(=O)—(CH$_2$)$_6$—OCH$_3$ or —C(CH$_3$)$_2$—COO—(CH$_2$)$_3$—CH$_3$.

$C_1$–$C_{24}$Alkylene interrupted by O is, for example, $C_4$alkylene interrupted by O such as especially —CH$_2$—CH$_2$—O—CH$_2$—CH$_2$—. $C_1$–$C_{24}$Alkylene interrupted twice by O is, for example, $C_6$alkylene interrupted by O, such as especially —CH$_2$—CH$_2$—O—CH$_2$—CH$_2$—O—CH$_2$—CH$_3$. $C_1$–$C_{24}$Alkylene substituted by oxo is, for example, $C_2$alkylene substituted by oxo, such as especially —C(=O)—CH$_2$—. $C_1$–$C_{24}$Alkylene substituted by oxo and interrupted by O is, for example, $C_8$alkylene interrupted by O, such as especially —(CH$_2$)$_3$—O—C(=O)—C(CH$_3$)$_3$, —C(=O)—(CH$_2$)$_6$—OCH$_2$— or —C(CH$_3$)$_2$—COO—(CH$_2$)$_3$—CH$_2$—, or preferably, for example, —O—($C_1$–$C_6$alkylene)—COO($C_1$–$C_6$alkyl), for example —O—CH$_2$—COOCH$_3$, —O—(CH$_2$)$_2$—COOCH$_3$, —O—(CH$_2$)$_3$—CO—CH$_3$, or —O—($C_1$–$C_6$alkylene)—COOH, for example —O—CH$_2$—COOH, —O—(CH$_2$)$_2$—COOH.

Mono- or poly-substitution by halogen, hydroxy, oxo or cyano and interruption one or more times by O, S or N normally alter the chemical reactivity of an alkyl, alkenyl or alkylene group only to a negligible extent. The person skilled in the art will therefore recognise further possible variations without any difficulty.

$C_5$–$C_{12}$Cycloalkyl is, for example, cyclopentyl, cyclohexyl, cycloheptyl, cyclooctyl, cyclononyl, cyclodecyl, cycloundecyl or cyclododecyl, preferably cyclopentyl, cyclohexyl or cycloheptyl.

Preferred as aralkyl and aryl is $C_7$–$C_{25}$aralkyl, such as $C_9$–$C_{13}$aralkyl, $C_7$–$C_{12}$aralkyl or $C_6$–$C_{12}$aryl. $C_7$–$C_{12}$Aralkyl is, for example, benzyl, 2-benzyl-2-propyl, β-phenyl-ethyl, 9fluorenyl, α,α-dimethylbenzyl, ω-phenyl-butyl or ω,ω-dimethyl-ω-phenyl-butyl.

$C_6$–$C_{12}$Aryl is, for example, phenyl, 1-naphthyl, 2-naphthyl, 4-biphenylyl or 2-fluorenyl.

$A_5$–$A_{18}$Heteroaryl is a mono-unsaturated heterocyclic structure of from 5 to 18 atoms selected from C, N, O and S, that contains at least 6 conjugated π-electrons. For example, $A_5$–$A_{18}$heteroaryl is thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythiinyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, and is preferably a mono- or bi-cyclic heteroaromatic radical.

Halogen is chlorine, bromine, fluorine or iodine, preferably fluorine or chlorine.

A polycycle is, for example, a condensed and/or bridged aromatic or alicyclic ring system that may be interrupted by hetero atoms such as O, S, N or P, such as, for example, octahydroquinolizine or tetradecahydroacridine.

$C_1$–$C_{12}$Alkyl or $C_2$–$C_{12}$alkenyl mono- or poly-substituted by halogen, hydroxy, oxo, $C_1$–$C_{12}$alkoxy or by cyano is, for example, 2-chloro-ethyl, trifluoromethyl, pentafluoroethyl, β,β,β-trifluoroethyl, trichlorovinyl, ω-chloro-propyl, ω-bromo-butyl, perfluorohexyl, perfluorododecyl, 2-hydroxy-ethyl, 2-methoxy-ethyl, 2-ethoxy-ethyl, 2-butoxy-ethyl, 2,3-dihydroxypropyl, 2,3-dimethoxy-propyl, or 2-cyano-ethyl, preferably trifluoromethyl, 2-hydroxy-ethyl, 2-methoxy-ethyl, 2-ethoxy-ethyl or 2-cyano-ethyl.

Special preference is given to a compound of the formula

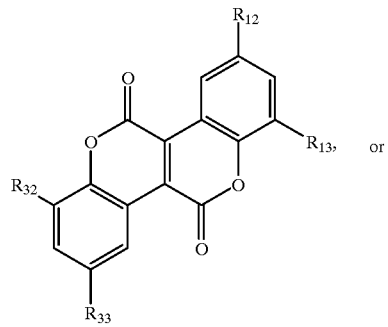

(XVII)

or

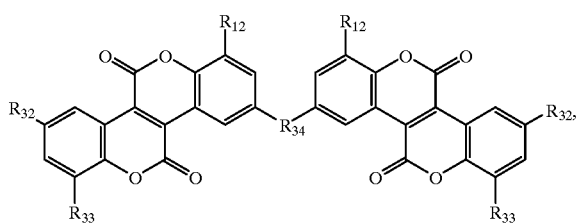

(XVIII)

a bis-dibenzonaphthyrone of the formula wherein
$R_{12}$, $R_{13}$, $R_{32}$ and $R_{33}$ are each independently of the others hydrogen, halogen, $NO_2$,
$R_{14}$, $OR_{14}$, $SR_{14}$ especially $OC_9$–$C_{18}$alkyl or $SC_9$–$C_{18}$alkyl, and $R_{34}$ is a single bond, $C_1$–$C_{24}$alkylene or $C_5$–$C_{12}$cycloalkylene, wherein $R_{14}$ is $C_1$–$C_{25}$alkyl which is unsubstituted or mono- or poly-substituted by oxo, cyano, $COOR_{16}$, $OCOR_{16}$ or by $COO^-X1^+$ and which may be uninterrupted or interrupted one or more times by O, especially ($C_1$–$C_{12}$alkyl)—$COOR_{16}$, or $C_6$–$C_{10}$aryl or $C_7$–$C_{10}$aralkyl each unsubstituted or mono- or poly-substituted by halogen, nitro, cyano, $OR_{16}$, $NR_{16}R_{17}$, $CONR_{16}R_{17}$, $COOR_{16}$, $OCOR_{16}$, $NR_{18}COR_{16}$ or by $NR_{18}COOR_{16}$;

$X1^+$ is a cation $Na^+$, $K^+$, $Mg^{++}_{1/2}$, $Ca^{++}_{1/2}$, $Zn^{++}_{1/2}$, $Al^{+++}_{1/3}$ or $[NR_{16}R_{17}R_{18}R_{19}]^+$; and $R_{16}$ and $R_{17}$ independently of each other are hydrogen, $C_6$–$C_{10}$aryl, $C_7$–$C_{10}$aralkyl, or $C_1$–$C_8$-alkyl which is unsubstituted or mono- or poly-substituted by halogen, hydroxy or by $C_1$–$C_4$-alkoxy; or $R_{16}$ and $R_{17}$ together with the common N are pyrrolidine, piperidine, piperazine or morpholine each unsubstituted or mono- to tetra-substituted by $C_1$–$C_4$alkyl; and $R_{18}$ and $R_{19}$ independently of each other are hydrogen, $C_1$–$C_{12}$alkyl, $C_6$–$C_{10}$aryl or $C_7$–$C_{10}$-aralkyl.

More special preference is given to the use of a compound of the formula

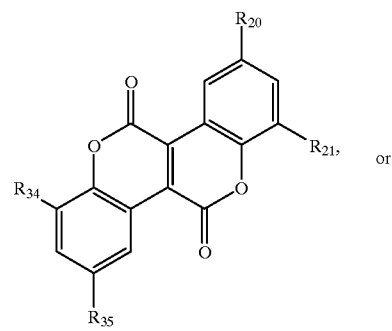

(XIX)

or a bis-dibenzonaphthyrone of the formula

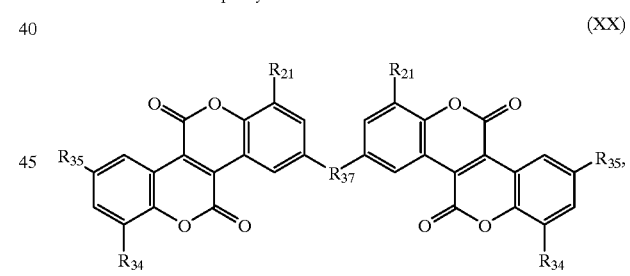

(XX)

wherein
$R_{20}$, $R_{21}$, $R_{34}$ and $R_{35}$ are each independently of the others hydrogen, chlorine, $R_{22}$, $OR_{22}$, especially $OC_2H_5COOCH_3$, $SR_{22}$, especially —$OC_9$–$C_{18}$alkyl or —$SC_9$–$C_{18}$alkyl, and $R_{37}$ is a single bond, $C_1$–$C_8$alkylene or $C_5$–$C_6$cycloalkylene, $R_{22}$ is $C_1$–$C_{25}$alkyl which is unsubstituted or mono- or poly-substituted by oxo, cyano, $COOR_{27}$, $OCOR_{27}$ or by $COO^-X2^+$ and which may be uninterrupted or interrupted one or more times by O, such as especially —O—$CH_2COOCH_3$, $C_2H_5COOH$, $C_2H_5COO$ ($C_1$–$C_{12}$alkyl), or is $C_6$–$C_{10}$aryl or $C_7$–$C_{10}$aralkyl, $X2^+$ is a cation $Na^+$, $K^+$, $Mg^{++}_{1/2}$, $Ca^{++}_{1/2}$, $Zn^{++}_{1/2}$, $Al^{+++}_{1/3}$ or $[NR_{24}R_{25}R_{26}R_{27}]^+$, $R_{24}$, $R_{25}$ and $R_{26}$ independently of one another are hydrogen, $C_1$–$C_{12}$alkyl or phenyl, and $R_{27}$ is hydrogen, $C_1$–$C_8$alkyl, $C_6$–$C_{10}$aryl or $C_7$–$C_{10}$aralkyl.

Most especially preferred is

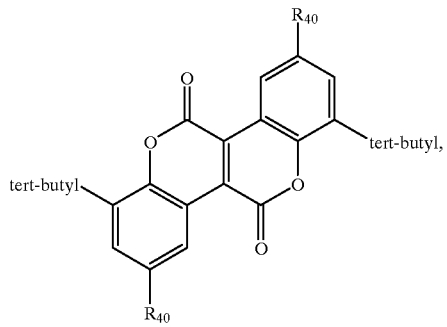

(LXIII)

wherein $R_{40}$ is tert-butyl, $OCH_3$, $C_2H_5COOH$ or $C_2H_5COO$ ($C_1$–$C_{12}$alkyl), especially tert-butyl, $OCH_3$ or $C_2H_5COOCH_3$.

Dibenzonaphthyrones may occur in various crystal modifications, as described by H. D. Becker et al., in Aust. J. Chem., 38(1), 97–110, 1985. In the case of polymorphism, in principle any crystal modification is suitable as a colourant.

The invention further relates to a process for the preparation of dibenzonaphthyrone of the formula

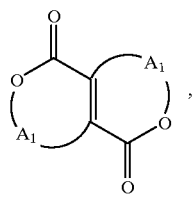

(XXIII)

which comprises dehydrating a compound of the formula

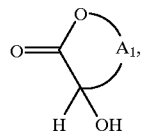

(XXIa)

or a tautomer thereof, to form isoxindigo of formula (XXIIa)

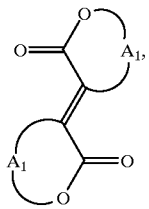

(XXIIa)

and subsequently isomerising, it also being possible for formula (XXIII) to represent compounds of formulae (II) to (XV).

The invention further relates to a process for the preparation of a mixture consisting of dibenzonaphthyrones of the formulae

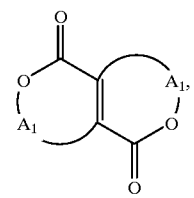

(XXIII)

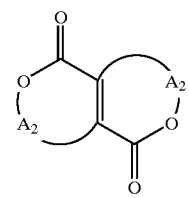

(XXIV)

and

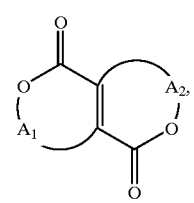

(XXV)

wherein $A_1$ and $A_2$ are different, which comprises dehydrating a mixture of compounds of the formulae

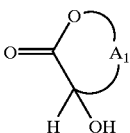

(XXIa)

and

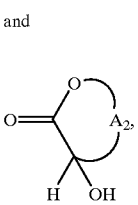

(XXIb)

or tautomers thereof, to form a mixture consisting of isoxindigos of the formulae

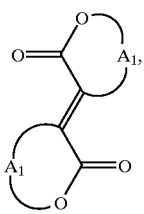

(XXIIa)

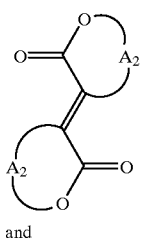
(XXIIb)

and

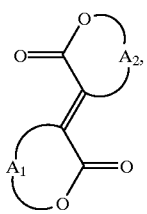
(XXIIc)

and subsequently isomerising, it also being possible for formulae (XXIII), (XXIV) and (XXV) to represent compounds of formulae (II) to (XV).

The compounds of formulae (XXIa) and (XXIb) and tautomers thereof are known from U.S. Pat. No. 5,614,572. It is not necessary to isolate the compound of formula (XXIa) or (XXIb); rather, the reaction mixture obtained in U.S. Pat. No. 5,614,572 can advantageously be further reacted directly.

A mixture of a compound of formula (XXIa) and a compound of formula (XXIb) usually consists of a molar ratio of the two compounds in the range of from 100:0.1 to 0.1:100, preferably from 90:10 to 10:90, especially from 95:5 to 5:95, and there is also especially preferred the molar mixing ratio of 1:1. The mixtures are generally prepared from the individual 3-hydroxy-benzofuranonyl compounds by prior mixing, in accordance with generally known methods, or are obtainable directly from a mixed synthesis of two differently substituted phenols with glyoxylic acid.

The dehydration can be performed thermally, for example at from 363 to 623K, preferably from 373 to 573 K, in an inert solvent, where appropriate with the addition of a protonic mineral or organic acid, a Lewis acid or an acid earth (such as, for example, Fulcat, montmorillonite, ion-exchanger). Where used, an amount of from 0.01 to 250 mol %, preferably from 1 to 10 mol %, based on the compound of formula (XVIa) or on the molar sum of the compounds (XXIa) and (XXIb), normally suffices. The dehydration is preferably carried out by removing water azeotropically from the reaction mixture using a water separator, with vigorous stirring and refluxing, where appropriate under reduced or elevated pressure.

The dehydration can also be performed chemically, the compound of formula (XXIa), or the compounds of formulae (XXIa) and (XXIb), first being reacted with an equimolar amount of an electrophilic reagent and then an acid being eliminated from the resulting product, for example at from 253 to 523 K, preferably at from 323 to 473 K, in an inert solvent, where appropriate with the addition of an organic base, such as, for example, triethylamine, a dialkylaniline, 1,8-diazabicyclo[5.4.0]undec-7-ene (DBU), 1,4-diazabicyclo[2.2.2]octane (DABCO), pyridine, an alkylpyridine, 4-dimethylaminopyridine (DMAP) or quinoline. An amount of from 0.01 to 250 mol %, preferably from 0.1 to 50 mol %, based on the compound of formula (XXIa), or on the compounds of formulae (XXIa) and (XXIb), normally suffices in that case. If, however, the acid to be eliminated is not volatile under the elimination conditions, it is advantageous to use at least 100 mol % of base, based on the compound of formula (XXIa) or on the compounds of formulae (XXIa) and (XXIb). The acid can thereby be eliminated even at a lower temperature.

As inert solvent it is possible to use, for example, an organic solvent that is unsubstituted or mono- or poly-substituted by halogen or nitro, such as $C_7$–$C_{25}$aralkyl, especially toluene, $C_9$–$C_{13}$aralkyl, or $C_6$–$C_{24}$aryl unsubstituted or mono- or poly-substituted by halogen or nitro, such as 1,2-dichlorobenzene, or $C_1$–$C_{24}$alkyl unsubstituted or mono- or poly-substituted by halogen or nitro, such as dichloroethane.

Suitable electrophilic reagents are, for example, methyl and ethyl esters of mineral acids, such as dimethyl sulfate or dimethylphosphonate, or organic or inorganic acid chlorides, such as thionyl chloride, phosgene, methanesulfonyl chloride, mesyl chloride, tosyl chloride or acetyl chloride, or anhydrides, such as acetic anhydride. A preferred electrophilic reagent is thionyl chloride.

The subsequent isomerisation can be carried out thermally and/or with base catalysis.

In a preferred embodiment, the isomerisation of the compounds of formulae (XXIIa), or (XXIIc), or (XXIIa), (XXIIb) and (XXIIc) to form (I) is usually base-catalysed.

Preference is given to the use of organic bases, such as, for example, tertiary amine bases, such as triethylamine, a dialkylaniline, 1,8-diazabicyclo[5.4.0]undec-7-ene (DBU), 1,4-diazabicyclo[2.2.2]octane (DABCO), or an aromatic nitrogen base, such as pyridine, alkylpyridine, dimethylaminopyridine (DMAP) or quinoline, preferably triethylamine, pyridine or quinoline, more preferably triethylamine or pyridine and most preferably pyridine.

The isomerisation according to the invention is advantageously carried out in the presence of solvents, especially protic, polar solvents, such as an alcohol, such as, for example, a $C_1$–$C_6$alcohol.

The isomerisation is usually carried out at elevated temperature, normally in the boiling temperature range of the solvent used.

The reaction can be observed by hypsochromic colour change. The end of the reaction normally lies in the range of from 1 to 40 hours, whereafter the colour no longer changes.

The dibenzonaphthyrone can be further processed in the customary manner; for example the crude product is filtered off, where appropriate washed, dried and, where appropriate, sieved.

The invention further relates to a process for the preparation of dibenzonaphthyrone of formulae (I) to (XV) by condensation of 3-oxo-furanonyl with 3-methylene-furanonyl compounds, which comprises condensing a 3-methylene-furanonyl compound of formula (XXXX)

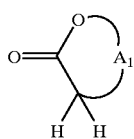

with a 3oxo-furanonyl compound of formula (XXXXI)

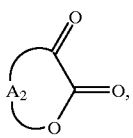

wherein $A_1$ and $A_2$ are different, using organic or inorganic acids or bases, to form isoxindigos of the formula

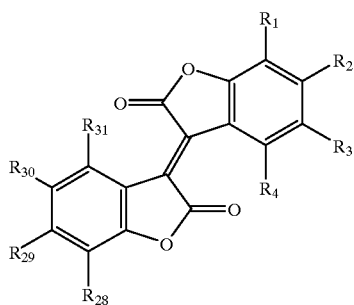
(XXXXIIa)

or

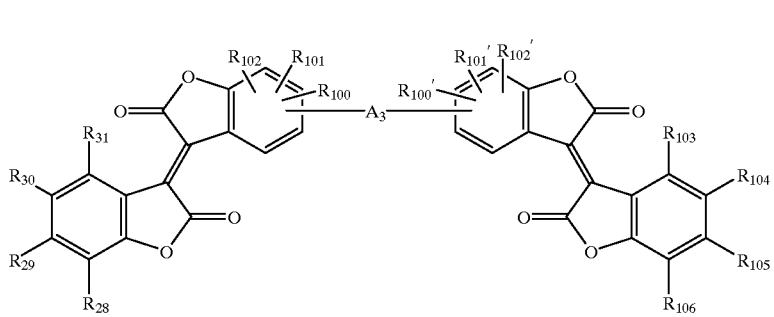
(XXXXIIb)

and subsequently isomerising.

The reaction is usually started by bringing a 3-methylene-furanonyl compound into contact with a 3-oxo-furanonyl compound and the condensation catalyst in accordance with methods known per se, for example by mixing the starting materials together or adding one of the starting materials dropwise to the other as described, for example, by J. N. Chaterjea in J. Indian Chem. Soc., 36, 70 (1959). In that literature reference, however, the condensation catalyst used is phosphorus tribromide which is ecologically harmful.

Acids or bases may be used as the condensation catalyst. For example, it is possible to use inorganic acids, such as hydrochloric or sulfuric acid, organic acids, such as arylsulfonic acids, especially ptoluenesulfonic acid, or alkanoic acids, formic acid or acetic acid, especially trifluoroacetic acid, and Lewis acids. It is possible to use as bases, for example, organic nitrogen bases, such as triethylamine, piperidine, pyridine, morpholine, or aliphatic alcoholates, such as, for example, methanolate, ethanolate, propanolate or butanolate, or aromatic alcoholates, such as, for example, phenolate.

As solvents it is possible to use organic acids, such as, for example, acetic acid, or alcohols, such as, for example, methanol, ethanol, propanol or hexanol, or hydrocarbons, such as, for example, hexane, heptane, or also ethers, such as, for example, tetrahydrofuran, diethyl ether or dioxane.

The molar ratio of 3-methylene-furanonyl to 3-oxo-furanonyl is normally selected to be in the range of from 1:1 to 3:1 and, preferably, the molar ratio is 1:1.

The molar ratio of the condensation catalyst to 3-oxo-furanonyl is normally selected to be in the range of from 0.001:1 to 5:1, preferably in the range of from 0.001:1 to 1:1 and especially in the range of from 0.001:1 to 0.05:1.

The reaction temperature selected is preferably a temperature at which the reaction mixture boils; it is in the range of the boiling temperature of the solvent used.

The reaction mixture can be worked up by the customary methods, such as, for example, by the addition of water and subsequent repeated extraction of the crude product with an organic solvent, such as toluene. The organic phase containing the crude product can be washed with water and then concentrated by evaporation. If desired, the crude product is combined with methanol and subsequently filtered, the product being obtained as the filter residue.

The starting materials for that process are prepared analogously to known processes. 3-Methylene-furanonyl compounds can be prepared, for example, analogously to the procedure of H.-D. Becker, K. Gustafsson, J.Org.Chem. 42, 2966 (1977) from phenols by reaction with glyoxal. 3-Oxo-furanonyl compounds obtained by oxidation of 3-hydroxy-furanonyl compounds can be prepared, for example, according to generally known methods of oxidising hydroxy compounds to keto compounds. Those methods are described, for example, in Houben-Weyl, Methoden der Organischen Chemie, 4th edition, Vol. 4/1a & 4/1b. In J. Org. Chem., 56, 6110 (1991), Z-Ma, J. M. Bobbitt describe oxidation using nitroxides. 3-Hydroxy-furanonyl compounds can be prepared analogously to the procedure for 3-hydroxy-benzofuranones which is described in U.S. Pat. No. 5,614,572.

Preferably, the bis-isoxindigos (IIb) are prepared from bis-3-oxo-furanonyl compounds of the formula (XXXII)

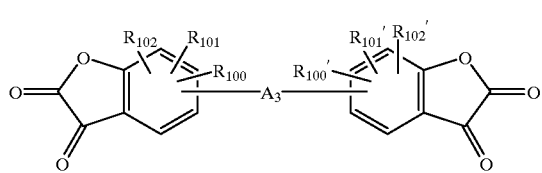

or from bis-3-methylene-furanonyl compounds of the formula (XXXIII)

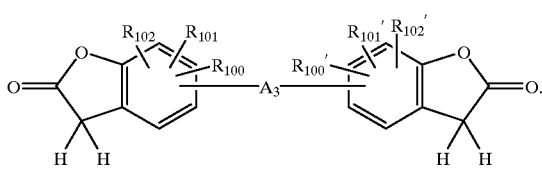

Preference is given to preparation from bis-3-oxo-furanonyl compounds (XXXII) by reaction with a 3-methylene-furanonyl compound (XXXIII) or, if desired, with a mixture of two differently substituted 3-methylene-furanonyl compounds (XXXIII).

Dibenzonaphthyrones are also obtainable from isoxindigos that isomerise, for example, during the process for colouring/pigmenting high-molecular-weight organic material, preferably at elevated temperatures.

The present invention further relates to compositions consisting of from 2 to 10 dibenzonaphthyrones of formulae (I) to (XV), preferably 2 or 3 compounds of formulae (I) to (XV).

If the composition consists of three compounds, these may be especially compounds of the formulae (XXIII)

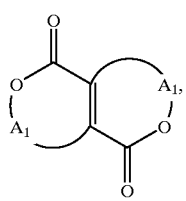

(XXIV)

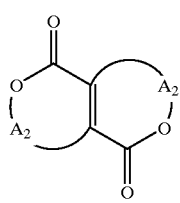

and (XXV)

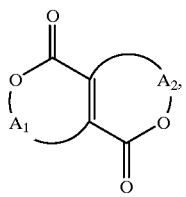

wherein $A_1$ and $A_2$ are different and the compounds of formulae (XXIII), (XXIV) and (XXV) also represent dibenzonaphthyrone of the formulae (II) to (XV).

The molar ratio of the compositions consisting of dibenzonaphthyrones of formulae (XXIII), (XXIV) and (XXV) is usually in the range of from 98:1:1 to 1:98:1 or 1:1:98, preferably in the range of 25:50:25 based on (XXIII):(XXIV):(XXV) and, in the case of two dibenzonaphthyrones, usually in the range of from 99:1: to 1:99.

The compositions consisting of from 2 to 10 dibenzonaphthyrones of formulae (I) to (XV) can be prepared from the individual compounds by mixing methods known per se or, in the case of three-component compositions, also by direct synthesis, which is described above.

The present invention further relates to a process for the mass-colouring/pigmenting of organic or inorganic, high-molecular-weight or low-molecular-weight material, especially high-molecular-weight organic material, which comprises admixing at least one dibenzonaphthyrone of formulae (I) to (XV), preferably from 2 to 10, and especially 2 or 3 compounds, with the organic or inorganic, high-molecular-weight or low-molecular-weight material, especially high-molecular-weight organic material, before processing thereof.

If three compounds are admixed, these are preferably (XXIII), (XXIV) and (XXV).

The invention further relates, therefore, to a substance composition comprising an organic or inorganic, high-molecular-weight or low-molecular-weight material, especially high-molecular-weight organic material, and at least one compound of formulae (I) to (XV) or a composition consisting of compounds of formulae (I) to (XV) in a colour-producing amount, normally in the range of from 0.01 to 70% by weight, especially from 0.01 to 30% by weight, preferably from 0.01 to 10% by weight, based on the organic or inorganic, high-molecular-weight or low-molecular-weight material.

The present invention further relates to the use of the compounds of formulae (I) to (XV) individually as colourants or fluorescent agents, especially for colouring or pigmenting organic or inorganic, high-molecular-weight or low-molecular-weight material, especially high-molecular-weight organic material. It is also possible, however, for the compositions according to the invention comprising compounds of formulae (I) to (XV) to be used in the form of mixtures, solid solutions or mixed crystals. Compounds of formulae (I) to (XV) can also be combined with colourants of another chemical class, for example with dyes or pigments, for example those selected from the group of the diketopyrrolopyrroles, quinacridones, perylenes, dioxazines, anthraquinones, indanthrones, flavanthrones, indigos, thioindigos, quinophthalones, isoindolinones, isoindolines, phthalocyanines, metal complexes, azo pigments and azo dyes.

Depending on the nature of their substituting and on the polymer to be coloured, the compounds of formulae (I) to (XV) can be used in the form of polymer-soluble dyes or in the form of pigments. In the latter case, it is advantageous to convert the products obtained in the synthesis into a finely dispersed form. That can be done in a manner known per se. Depending on the compound and the intended use, it proves advantageous to use the colourants as toners or in the form of preparations.

The high-molecular-weight material may be organic or inorganic and may be synthetic and/or natural material. The high-molecular-weight organic material usually has an average molecular weight of $10^5$–$10^7$ g/mol. It may be, for example, a natural resin or a drying oil, rubber or casein or a modified natural material, such as chlorinated rubber, oil-modified alkyd resins, viscose, or a cellulose ether or ester, such as ethylcellulose, cellulose acetate, propionate or butyrate, cellulose acetobutyrate or nitrocellulose, but is especially a completely synthetic organic polymer (duroplasts and thermoplasts) as may be obtained by polymerisation, for example by polycondensation or polyaddition. The class of polymers includes, for example, polyolefins, such as polyethylene, polypropylene, polyisobutylene, and substituted polyolefins, such as polymerisates of monomers such as vinyl chloride, vinyl acetate, styrene, acrylonitrile, acrylates, methacrylates, fluoropolymers, such as polyfluoroethylene, polytrifluorochloroethylene or tetrafluoroethylene/hexafluoropropylene mixed polymerisate, and copolymerisates of the mentioned monomers, especially ABS (acrylonitrile/butadiene/styrene) or EVA (ethylene/vinyl acetate). From the group of polyaddition and polycondensation resins it is possible to use, for example, condensation products of formaldehyde with phenols, the so-called phenoplasts, and condensation products of formaldehyde and urea or thiourea, also melamine, the so-called aminoplasts, and the polyesters used as surface coating resins, either saturated, such as alkyd resins, or unsaturated, such as maleic resins, and also linear polyesters, polyamides, polyurethanes, polycarbonates, polyphenylene oxides or silicones, and silicone resins. The mentioned high-molecular-weight compounds may be present individually or in mixtures in the form of kneadable compounds, melts or in the form of spinning solutions. They may also be present in the form of their monomers or in the polymerised state in dissolved form as film-formers or binders for paints or printing inks, such as, for example, boiled linseed oil, nitrocellulose, alkyd resins, melamine resins and urea-formaldehyde resins or acrylic resins.

Low-molecular-weight materials are, for example, mineral oils, waxes or lubricating greases.

The present invention further relates, therefore, to the use of the compounds of formulae (I) to (XV) and of the compositions according to the invention consisting of compounds of formulae (I) to (XV) for the production of inks, for printing inks in printing processes, for flexographic printing, screen printing, the printing of packaging, security colour printing, intaglio printing or offset printing, for preliminary printing stages and for textile printing, for office and home use or for graphics, such as, for example, for paper goods, for ball-point pens, felt-tip pens, fibre-tip pens, paperboard, wood, (wood) stains, metal, stamp pads or inks for impact printing processes (with impact printing ink ribbons), for the production of colourants, for paints, for use in industry or advertising, for textile decoration and industrial labelling, for roll coating or powder coating compositions or for automobile paints, for high-solids (low-solvent), water-containing or metallic paints or for pigmented formulations for aqueous paints, for mineral oils, lubricating greases or waxes, for the production of coloured plastics for coatings, fibres, plates or moulded substrates, for the production of non-impact printing material for digital printing, for the thermal wax-transfer printing process, the ink-jet printing process or for the thermal transfer printing process, and also for the production of colour filters, especially for visible light in the range of from 400 to 700 nm, for liquid crystal displays (LCDs) or charge-coupled devices (CCDs) or for the production of cosmetics or for the production of polymeric colour particles, toners, dry copy toners, liquid copy toners or electrophotographic toners.

The present invention further relates to the use of substance compositions comprising an organic or inorganic, high-molecular-weight or low-molecular-weight material, especially high-molecular-weight organic material, and at least one compound of formulae (I) to (XV) or a composition consisting of compounds of formulae (I) to (XV) in a colour-producing amount for the production of inks or colourants for paints, printing inks, mineral oils, lubricating greases or waxes, or coloured or pigmented plastics, non-impact printing material, colour filters, cosmetics or toners.

The present invention further relates to inks comprising high-molecular-weight organic material and a colour-producing amount of the compound (I) to (XV) or of the composition consisting of compounds of formulae (I) to (XV).

For example, the inks can be produced by mixing the compounds according to the invention with polymeric dispersants.

The mixing of the compounds according to the invention with the polymeric dispersant is preferably carried out by generally known mixing methods, such as stirring or mixing, and the use of an intensive mixer, such as an Ultraturax, is especially to be recommended.

When mixing the compounds according to the invention with polymeric dispersants, a water-dilutable organic solvent is advantageously used.

The weight ratio of the compounds according to the invention to ink is advantageously selected to be in the range of from 0.0001 to 75% by weight, preferably from 0.001 to 50% by weight, based on the total weight of the ink.

The present invention therefore relates also to a process for the production of inks which comprises mixing high-molecular-weight organic material with a colour-producing amount of the compound of formulae (I) to (XV) or compositions thereof consisting of compounds of formulae (I) to (XV).

The present invention further relates to colourants comprising high-molecular-weight organic material and a compound according to the invention of formulae (I) to (XV), or a composition according to the invention consisting of compounds of formulae (I) to (XV), in a colour-producing amount.

The present invention relates, in addition, to a process for the preparation of colourants which comprises mixing a high-molecular-weight organic material and a colour-producing amount of the compound according to the invention of formulae (I) to (XV) or composition according to the invention consisting of compounds of formulae (I) to (XV).

The present invention further relates to coloured or pigmented plastics or polymeric coloured particles comprising high-molecular-weight organic material and compound (I)

to (XV), or composition consisting of compounds of formulae (I) to (XV), in a colour-producing amount.

The present invention relates, in addition, to a process for the preparation of coloured or pigmented plastics or polymeric coloured particles which comprises mixing together a high-molecular-weight organic material and a colour-producing amount of the compound of formulae (I) to (XV) or composition consisting of compounds of formulae (I) to (XV).

The colouring of high-molecular-weight organic substances with the colourants of formulae (I) to (XV) or the compositions consisting of compounds of formulae (I) to (XV) is carried out, for example, by mixing such a colourant, optionally in the form of a master batch, into those substrates using roll mills or mixing or grinding apparatus, whereby the colourant is dissolved or finely distributed in the high-molecular-weight material. The high-molecular-weight organic material with the admixed colourant is then processed according to procedures known per se, such as, for example, calendering, compression moulding, extrusion moulding, coating, spinning, casting or injection-moulding, whereby the coloured material acquires its final form. Admixing of the colourant can also be carried out immediately prior to the actual processing step, for example by continuously metering a powdered colourant according to the invention and a granulated high-molecular-weight organic material, and optionally also additional ingredients, such as additives, directly into the inlet zone of an extruder simultaneously, where mixing takes place just before the processing operation. In general, however, prior mixing of the colourant into the high-molecular-weight organic material is preferred, since more uniform results can be obtained.

It is often desirable for the purpose of producing non-rigid mouldings or reducing the brittleness thereof to incorporate so-called plasticisers into the high-molecular-weight compounds before shaping. There may be used as plasticisers, for example, esters of phosphoric acid, phthalic acid or sebacic acid. In the process according to the invention, the plasticisers can be incorporated into the polymers before or after the incorporation of the colourant. In order to obtain different colour shades it is also possible to add to the high-molecular-weight organic substances, in addition to the compounds of formulae (I) to (XV) or compositions according to the invention consisting of compounds of formulae (I) to (XV), any desired amounts of constituents such as white, coloured or black pigments.

For the colouring of paints and printing inks, the high-molecular-weight organic materials and the compounds of formulae (I) to (XV) or the compositions according to the invention consisting of compounds of formulae (I) to (XV), optionally together with additional ingredients, such as fillers, dyes, pigments, siccatives or plasticisers, are finely dispersed or dissolved in a common organic solvent or solvent mixture. That procedure may comprise dispersing or dissolving each individual component on its own or dispersing or dissolving several components together and only then combining all the components. Processing is carried out in accordance with customary methods, for example by spraying, film-spreading or one of the many printing methods, whereupon the paint or printing ink is advantageously cured thermally or by irradiation, optionally after previous drying.

When the high-molecular-weight material to be coloured is a paint, it may be a conventional paint or a special paint, for example an automobile finish, preferably a metal-effect finish containing, for example, metal or mica particles.

Preference is given to the colouring of thermoplastics, especially also in the form of fibres, and printing inks.

Preferred high-molecular-weight organic materials that can be coloured according to the invention are, very generally, polymers having a dielectric constant $\geq 2.5$, especially polyesters, polycarbonate (PC), polystyrene (PS), polymethylmethacrylate (PMMA), polyamide, polyethylene, polypropylene, styrene/acrylonitrile (SAN) or acrylonitrile/butadiene/styrene (ABS). More especially preferred are polyesters, polycarbonate, polystyrene and PMMA. Most especially preferred are polyesters, polycarbonate and PMMA, especially aromatic polyesters that can be obtained by polycondensation of terephthalic acid, such as, for example, polyethylene terephthalate (PET) or polybutylene terephthalate.

They can be used in the form of their monomers or copolymers or in the polymerised state in dissolved form as film formers or binders for paints that can be used for the decoration of metal or for decorative colour finishes, and for printing inks used, for example, in the ink-jet printing process, or also for wood stains.

Special preference is also given to the colouring of mineral oils, lubricating greases and waxes with the compounds according to the invention.

The present invention also relates to mineral oils, lubricating greases and waxes comprising high-molecular-weight organic material and a compound of formulae (I) to (XV), or compositions consisting of compounds of formulae (I) to (XV), in a colour-producing amount.

The present invention also relates to a process for the preparation of mineral oils, lubricating greases and waxes, which comprises mixing high-molecular-weight organic material with a colour-producing amount of the compound of formulae (I) to (XV), or compositions thereof consisting of compounds of formulae (I) to (XV).

The present invention also relates to non-impact printing material comprising high-molecular-weight organic material and a compound of formulae (I) to (XV), or compositions consisting of compounds of formulae (I) to (XV), in a colour-producing amount.

The present invention relates, in addition, to a process for the preparation of non-impact printing material, which comprises mixing together a high-molecular-weight organic material and a colour-producing amount of the compound of formulae (I) to (XV) or compositions consisting of compounds of formulae (I) to (XV).

The present invention further relates to a process for the production of colour filters comprising a transparent substrate and a red, a blue and a green coating applied thereto in any desired sequence, which comprises using for the production of the red, blue and green coatings a correspondingly coloured compound of formulae (I) to (XV) or compositions comprising compounds of formulae (I) to (XV).

The different-coloured coatings are preferably arranged in such a pattern that they do not overlap over at least 5% of their respective surface area and, most preferably, do not overlap at all.

The colour filters can be coated, for example, using inks, especially printing inks, comprising the compounds or compositions according to the invention, or, for example, by mixing a compound or composition according to the invention with a chemically, thermally or photolytically structurable high-molecular-weight material (resist). The further production can be carried out, for example, analogously to EP-A 654 711, by application to a substrate, such as an LCD, subsequent photo-structuring and developing.

The invention further includes a transparent substrate coated with a red, a blue and a green coating each of a correspondingly coloured compound of formulae (I) to (XV), or composition consisting of compounds of formulae (I) to (XV), comprising pigmented high-molecular-weight organic material.

The sequence in which coating is carried out is not important as a rule. The different-coloured coatings are preferably arranged in such a pattern that they do not overlap over at least 5% of their respective surface area and, most preferably, do not overlap at all.

The present invention also includes colour filters comprising a transparent substrate and, applied thereto, a red, a blue and a green coating, each obtainable from a correspondingly coloured compound of formulae (I) to (XV) or from compositions comprising compounds of formulae (I) to (XV).

The present invention relates, in addition, to toners comprising high-molecular-weight organic material and a compound of formulae (I) to (XV), or compositions consisting of compounds of formulae (I) to (XV), in a colour-producing amount.

The present invention also relates to a process for the production of toners, which comprises mixing together a high-molecular-weight organic material and a colour-producing amount of the compound of formulae (I) to (XV) or compositions consisting of compounds of formulae (I) to (XV).

The present invention also relates to inks or colourants for paints, printing inks, mineral oils, lubricating greases or waxes, or coloured or pigmented plastics, non-impact printing material, colour filters, cosmetics or toners comprising high-molecular-weight organic material and compound (I) to (XV), or composition comprising an organic or inorganic, high-molecular-weight or low-molecular-weight material and at least one compound of formulae (I) to (XV), in a colour-producing amount.

In a special embodiment of the process according to the invention, toners, paints, inks or coloured plastics are produced by processing master batches of toners, paints, inks or coloured plastics in roll mills or mixing or grinding apparatus.

A colour-producing amount of the compound of formulae (I) to (XV) or of compositions consisting of compounds of formulae (I) to (XV) means in the present invention normally from 0.0001 to 99.99% by weight, preferably from 0.001 to 50% by weight and especially from 0.01 to 50% by weight, based on the total weight of the material coloured or pigmented therewith.

The coloured/pigmented high-molecular-weight materials obtained, such as, for example, plastics, fibres, paints and prints, are distinguished by very high colour intensity, high saturation, good fastness to overspraying, good migration-stability, good fastness to heat, light and weathering and by a high gloss and good IR reflectance behaviour.

The high economic efficiency of the process according to the invention compared with previous preparation processes for dibenzonaphthyrones makes those compounds commercially attractive. Dibenzonaphthyrones of formulae (I) to (XV) produce surprisingly brilliant colour finishes of high colour intensity, are additionally distinguished by a high degree of fluorescence and exhibit surprisingly good heat-stability and light-fastness properties in polar plastics. Despite very good solubilities, the dibenzonaphthyrones have surprisingly good migration properties in the coloured material. In mixtures comprising the compounds according to the invention, beautiful shades of colour are obtained. Especially advantageously, asymmetric dibenzonaphthyrones and bis-dibenzonaphthyrones enable further colour shades to be obtained and allow their solubility to be influenced by the choice of the substituting.

EXAMPLE 1

Preparation of hydroxybenzofuranone, 5,7-di-tert-butyl-3-hydroxy-3H-benzofuran-2-one 300 ml of toluene, 212 g of 97% by weight 2,4-di-tert-butyl-phenol (Fluka), 121.9 ml of 50% by weight aqueous glyoxylic acid (Fluka), and 40 g p-toluenesulfonic acid monohydrate (Fluka, Aldrich) are added in succession, with stirring, to a 1.5 litre multi-necked vessel equipped with stirrer, dropping funnel, water separator, condenser and thermometer. The reaction mixture is then refluxed vigorously while stirring well, during which the water present in the glyoxylic acid and the water of reaction of the first step separates. After a reflux time of approximately 3 hours, the separation of water ceases, leaving a homogeneous, slightly yellow solution of the hydroxybenzofuranone, 5,7-di-tert-butyl-3-hydroxy-3H-benzofuran-2-one.

EXAMPLE 2a

Dehydration to isoxindigo; in toluene with thionyl chloride and triethylamine

The reaction mixture from Example 1 is diluted with 40 ml of a linear $C_9$–$C_{13}$alkylbenzene that boils at 548–585 K (®Marlican, Hüls). Then, under normal pressure and at a heating-bath temperature of up to 415 K, approximately 200 ml of toluene are distilled off. At the end of the distillation, the internal temperature is approximately 393 K. The light-yellow, oily mixture is cooled to an internal temperature of approximately 60° C. and 13.9 ml of triethylamine are added thereto. 79.8 ml of thionyl chloride are then added dropwise from the dropping funnel sufficiently rapidly that the evolution of HCl and $SO_2$ remains vigorous yet controllable. The addition lasts approximately 75 min, and the internal temperature is 333–340 K. When the formation of gas has virtually subsided, the reaction mixture is stirred for a further hour at 373 K. The heating control of the heating bath is then increased to 473 K. The temperature of the reaction mixture rises to 459 K over a period of approximately 35 min, during which a further 105 ml of toluene distil off. At the same time, a vigorous stream of HCl gas escapes once more. If the evolution of gas is too violent, the heating rate is reduced accordingly. The mixture, which is already deep-red, is then stirred for a further 2 hours at 453–463 K. The thick, dark-red to black crystal suspension is cooled to approximately 423 K; 200 ml of n-butanol followed by 400 ml of ethanol are then added through the condenser. The crystal suspension is stirred under reflux for approximately a further hour, is then cooled to 273–278 K and filtered off. The crystal cake is washed with sufficient cold ethanol (approximately 600 ml) until the filtrate is clearly no longer brown-tinged but is faintly red in colour. The crystalline dye is then dried at 353 K/50 mbar, yielding 186.2 g (76.2% of the theoretical yield based on 2,3-di-tert-butyl-phenol) of fine, deep-red, shiny crystals of 5,7,5',7'-tetra-tert-butyl-[3,3']bibenzofuranylidene-2,2'-dione of formula (LIa).

| melting point: | 427–429 K.; | | |
| --- | --- | --- | --- |
| elemental analysis: | | % C | % H |
| | calc. | 78.65 | 8.25 |
| | found | 78.40 | 8.39 |

EXAMPLE 2b

Dehydration to isoxindigo; in 1,2-dichlorobenzene with thionyl chloride and 4-dimethylaminopyridine 10 g of 5,7-di-tert-butyl-3-hydroxy-3H-benzofuran-2-one (prepared as described in Ex. 1a of U.S. Pat. No. 5,614,572)

are placed in 25 ml of 1,2-dichlorobenzene, and 0.5 g of 4-dimethylaminopyridine and 3 ml of thionyl chloride are added thereto. The solution is then slowly heated to 373 K at such a rate that the evolution of HCl and $SO_2$ remains vigorous yet controllable. It is then stirred at that temperature for a further ½ hour. The temperature is then increased to reflux temperature. After 75 min, the 1,2-dichlorobenzene is distilled off, under reduced pressure at the end. The isoxindigo is crystallised out by adding 30 ml of acetonitrile to the residue, is filtered off, washed with acetonitrile and dried, yielding 6.8 g (73% of the theoretical yield) of 5,7,5',7'-tetra-tert-butyl-[3,3]bibenzofuranylidene-2,2'-dione of formula (LIa).

EXAMPLE 2c

Dehydration to isoxindigo; in toluene with thionyl chloride and N,N'-dimethylformamide 78.7 g of 5,7-di-tert-butyl-3-hydroxy-3H-benzofuran-2-one (prepared as in Ex. 2b) are placed in 150 ml of toluene, and 3 drops of dimethylformamide (DMF) and 45 ml of thionyl chloride are added thereto. The solution is then slowly heated to 373 K at such a rate that the evolution of HCl and $SO_2$ remains vigorous yet controllable. It is then stirred at that temperature for a further hour. Approximately 150 ml of liquid are then distilled off in order to remove the excess thionyl chloride. The residue is diluted with 480 ml of toluene and, at room temperature, 42 ml of triethylamine are added dropwise. The thick, red reaction mixture is then heated under reflux for 15 min. After cooling to room temperature, the triethylamine hydrochloride which has precipitated is filtered off, and the filtrate is washed with water and concentrated NaCl solution and concentrated to an oily consistency using a rotary evaporator. The isoxindigo is crystallised out by adding 225 ml of acetonitrile, is filtered off, washed with acetonitrile and dried, yielding 57.7 g (78.7% of the theoretical yield) of 5,7,5',7'-tetra-tert-butyl-[3,3']bibenzofuranylidene-2,2'-dione of formula (LIa).

EXAMPLE 3a

Dehydration to isoxindigo; in toluene with thionyl chloride/dimethylformamide and triethylamine 22 g of 7-tert-butyl-3-hydroxy-5-methyl-3H-benzofuran-2-one (prepared as described in Ex. 2 of U.S. Pat. No. 5,614,572) are placed in 50 ml of toluene, and 3 drops of DMF and 15 ml of thionyl chloride are added thereto. The solution is then slowly heated to 373 K at such a rate that the evolution of HCl and $SO_2$ remains vigorous yet controllable. It is then stirred at 373 K for a further hour. Approximately 50 ml of liquid are then distilled off in order to remove the excess thionyl chloride. The residue is diluted with 160 ml of toluene and, at room temperature, 14 ml of triethylamine are added dropwise. The thick, red reaction mixture is then heated under reflux for 30 min. After cooling to room temperature, the triethylamine hydrochloride which has precipitated is filtered off, and the residue is concentrated to an oily consistency using a rotary evaporator. The isoxindigo is crystallised out by adding 200 ml of acetonitrile, is filtered off, washed with acetonitrile and dried, yielding 11.6 g (57% of the theoretical yield) of 7,7'-di-tert-butyl-5,5'-dimethyl-[3,3']bibenzofuranylidene-2,2'-dione of formula (LIa).

melting point: 426–428 K;

$^1$H-NMR (CDCl$_3$, 300 MHz), δ [ppm]: 1.43 s/9H; 2.41 s/3H; 7.26 s/1H; 8.72 s/1H.

EXAMPLE 3b

Dehydration to isoxindigo; in dichlorobenzene with camphor-10-sulfonic acid 2.2 g of 7-tert-butyl-3-hydroxy-5-methyl-3H-benzofuran-2-one (prepared as in Ex. 3a) are boiled under reflux for 17 hours in 10 ml of 1,2-dichlorobenzene with 0.23 g of camphor-10-sulfonic acid. The red reaction mixture is then diluted with 20 ml of dichloromethane, washed with water and concentrated by evaporation using a rotary evaporator. The isoxindigo is crystallised out by adding 15 ml of methanol to the residue, is filtered off, washed with methanol and dried, yielding 0.77 g (38% of the theoretical yield) of 7,7'-di-tert-butyl-5,5'-dimethyl-[3,3']bibenzofuranylidene-2,2'-dione of formula (La).

EXAMPLE 3c

Dehydration to Isoxindigo by Thermal Treatment 2.2 g of 7-tert-butyl-3-hydroxy-5-methyl-3H-benzofuran-2-one (prepared as in Ex. 3a) are heated at 408 K for 3 hours in a flask equipped with a descending condenser. The red reaction mixture is then cooled to approximately 423 K, and the isoxindigo is crystallised out by adding 10 ml of methanol, is filtered off, washed with methanol and dried, yielding 0.55 g (27% of the theoretical yield) of 7,7'-di-tert-butyl-5,5'-dimethyl-[3,3']bibenzofuranylidene-2,2'-dione of formula (La).

EXAMPLE 4

Dehydration to isoxindigo; in toluene with thionyl chloride/N,N'-dimethylformamide and triethylamine 7.1 g of 3-hydroxy-5-methyl-7-(1,1,3,3-tetramethyl-butyl)-3H-benzofuran-2-one (U.S. Pat. No. 5,614,572, column 35, compound N° 111) are placed in 12.5 ml of toluene, and 3 drops of DMF and 2.7 ml of thionyl chloride are added thereto. The solution is then slowly heated to 373 K at such a rate that the evolution of HCl and $SO_2$ remains vigorous yet controllable. It is then stirred at 373 K for 1 hour. Approximately 12 ml of liquid are then distilled off in order to remove the excess thionyl chloride. The residue is diluted with 37.5 ml of toluene and, at room temperature, 3.5 ml of triethylamine are added dropwise. The thick, red reaction mixture is then heated to reflux temperature and boiled for 30 min. After cooling to room temperature, the triethylamine hydrochloride which has precipitated is filtered off, and the filtrate is concentrated to an oily consistency using a rotary evaporator. The isoxindigo is crystallised out by adding 25 ml of acetonitrile, is filtered off, washed with acetonitrile and dried, yielding 3.45 g (53% of the theoretical yield) of 5,5'-dimethyl-7,7'-bis(1,1,3,3-tetra-methyl-butyl)-[3,3'] bibenzofuranylidene-2,2'-dione of formula (LIIa).

melting point: 460–463 K;

$^1$H-NMR (CDCl$_3$,300 MHz), δ [ppm]: 0.75 s/9H; 1.52 s/6H; 1.94 s/2H; 2.41 s/3H; 7.27 s/1H; 8.75 s/1H.

EXAMPLE 5

Preparation of hydroxybenzofuran and Dehydration to isoxindigo; in toluene with thionyl chloride/ ®Marlican and triethylamine 42.7 g of 3-tert-butyl-4-hydroxyanisole (Fluka) are boiled with 38.5 g of 50% by weight aqueous glyoxylic acid and 0.2 g of p-toluenesulfonic acid in 75 ml of toluene for 90 min using a water separator. Then, at 373 K, 19 ml of thionyl chloride are added dropwise to the reaction mixture sufficiently rapidly that the evolution of HCl and $SO_2$ remains vigorous yet controllable. The reaction mixture is then stirred at 373 K for a further hour. Then 10 ml of ®Marlican and 3.3 ml of triethylamine are added. The temperature is then increased to 453 K over a period of 30 min while simultaneously distilling off 71 ml of toluene. After stirring at 453 K for a further 1.5 hours, the reaction mixture is cooled to 423 K, 50 ml of n-butanol and then 100 ml of ethanol are added thereto, and the reaction mixture is heated under reflux for 1 hour and then cooled to 273–278 K. The isoxindigo which has precipitated is filtered off, washed with ethanol and dried, yielding 17.2 g (33% of the theoretical yield) of 7,7'-di-tert-butyl-5,5'-dimethoxy-[3,3'] bibenzofuranylidene-2,2'-dione of formula (LIXa).

| melting point: | 617–621 K.; | | |
| elemental analysis: | | % C | % H |
| | calc. | 71.54 | 6.47 |
| | found | 71.44 | 6.51 |

EXAMPLE 6

Preparation of Hydroxybenzofuran and Dehydration to isoxindigo; in this case in toluene with thionyl chloride/triethylamine 2.8 g of 2-tert-butyl-4-chlorophenol [J. Amer. Chem. Soc. 78, 4604 (1956)] are heated under reflux with 2.45 g of 50% by weight aqueous glyoxylic acid and 50 mg of p-toluenesulfonic acid in 20 ml of 1,2-dichloroethane for 3¼ hours. A further 2.45 g of 50% by weight aqueous glyoxylic acid are then added and boiling is continued for 18 hours. The reaction mixture is then washed with water, dried over $MgSO_4$ and concentrated by evaporation using a rotary evaporator. Crystallisation of the residue from hexane yields 1.15 g of 7-tert-butyl-5-chloro-3-hydroxy-3H-benzofuran-2-one (melting point: 423–427 K). 1.1 g of that compound are placed in 5 ml of toluene with 1 ml of thionyl chloride and the reaction mixture is then slowly heated to 373 K at such a rate that the evolution of HCl and $SO_2$ remains vigorous yet controllable. The reaction mixture is then stirred at 373 K for a further hour. Approximately 5 ml of liquid are then distilled off in order to remove the excess thionyl chloride. The residue is diluted with 13 ml of toluene and, at room temperature, 0.6 ml of triethylamine is added dropwise thereto. The thick, red reaction mixture is then heated to reflux temperature and boiled for 45 min. After cooling to room temperature, the isoxindigo which has precipitated is filtered off, freed of triethylamine hydrochloride by washing with water and methanol and dried, yielding 0.47 g (46% of the theoretical yield) of 7,7'-di-tert-butyl-5, 5'-dichloro-[3,3']bibenzofuranylidene-2,2'-dione of formula (LIXa).

| melting point: | above 573 K.; | | |
| elemental analysis: | | % C | % H |
| | calc. | 64.73 | 4.98 |
| | found | 64.59 | 4.96 |

EXAMPLE 7

Pregaration of hydroxybenzofuran and Dehydration to isoxindigo; in 1,2-dichlorethane with thionyl chloride/N,N'dimethylformamide and triethylamine 32.5 g of 2,6-di-tert-butyl-4-phenylsulfanyl-phenol [Org. Chem. 38, 687 (1973)] are melted with 1.2 g of camphor-10-sulfonic acid at 393 K. A weak stream of nitrogen (~1 ml/min) is then passed through the stirred melt for 29 hours. The reaction mixture is then diluted with toluene, washed with water and concentrated by evaporation using a rotary evaporator. 10.8 g of oily 2-tert-butyl-4-phenyl-sulfanyl-phenol are obtained from the residue by column chromatography on silica gel (hexane/ethyl acetate 19:1). That oil is boiled under reflux with 6.84 g of 50% by weight aqueous glyoxylic acid and 50 mg of p-toluenesulfonic acid in 40 ml of 1,2-dichloroethane for 24 hours. A further 4 g of 50% aqueous glyoxylic acid are then added and boiling is continued for a further 5 hours. The reaction mixture is then washed with water, dried over $MgSO_4$ and concentrated by evaporation using a rotary evaporator. The addition of 20 ml of hexane to the residue causes 7-tert-butyl-3-hydroxy-5-phenylsulfanyl-3H-benzofuran-2-one to separate in the form of a viscous oil, which is removed and dried in vacuo (9.3 g). 2.45 g of that viscous oil are placed in 10 ml of toluene with 1.1 ml of thionyl chloride and 3 drops of DMF and the reaction mixture is then slowly heated to 373 K at such a rate that the evolution of HCl and $SO_2$ remains vigorous yet controllable. The reaction mixture is then stirred at 373 K for 1 hour. Approximately 10 ml of liquid are then distilled off in order to remove the excess thionyl chloride. The residue is diluted with 15 ml of toluene and, at room temperature, 1.1 ml of triethylamine are added dropwise thereto. The thick, red reaction mixture is then heated to reflux temperature and boiled for 45 min. After cooling, 20 ml of water are added. The organic phase is concentrated by evaporation and the isoxindigo is isolated therefrom by chromatography on silica gel (hexane/toluene 2:1), yielding 0.53 g (23% of the theoretical yield) of 7,7'-di-tert-butyl-5,5'-bis-phenylsulfanyl-[3,3']bibenzo-furanylidene-2,2'-dione of formula (LVIIIa).

| melting point: | 478–485 K.; | | |
| elemental analysis: | | % C | % H |
| | calc. | 72.95 | 5.44 |
| | found | 72.99 | 5.34 |

EXAMPLE 8

Preparation of hydroxybenzofuran and Dehydration to isoxindigo; in toluene with thionyl chloride/N, N'-dimethylformamide and triethylamine 18.7 g of 4-tert-butyl-2-(1-methyl-pentadecyl)-phenol (J.Amer.Chem.Soc., 74, 1952, 3599), 5.06 g of glyoxylic acid monohydrate and 0.05 g of p-toluenesulfonic acid are heated in 40 ml of 1 ,2-dichloroethane for 7 hours using a water separator. The reaction solution is then cooled, washed three times with 80 ml of water each time and freed of solvent using a rotary evaporator. 21.4 g of 5-tert-butyl-3-hydroxy-7-(1-methyl-pentadecyl)-3H-benzo-furan-2-one are obtained in the form of a yellowish oil. That yellowish oil is placed in 25 ml of toluene with 8 ml of thionyl chloride and 3 drops of DMF and the reaction mixture is then slowly heated to 373 K at such a rate that the evolution of HCl and $SO_2$ remains vigorous yet controllable. The reaction mixture is then stirred at that temperature for a further hour. Approximately 25 ml of liquid are then distilled off in order to remove the excess thionyl chloride. The residue is diluted with 80 ml of toluene and, at room temperature, 7 ml of triethylamine are added dropwise thereto. The thick, red reaction mixture is then heated under reflux for 30 min. After cooling to room temperature, the triethylamine hydrochloride which has precipitated is filtered off and the filtrate is concentrated to an oily consistency using a rotary evaporator. The isoxindigo is isolated from the residue, in the form of a waxy red mass, by chromatography on silica gel (hexane/ethyl acetate 99:1). 4.1 g (20% of the theoretical yield, based on 4-tert-butyl-2-(1-methyl-pentadecyl)-phenol) of 5,5'-di-tert-butyl-7,7'-bis(1-methyl-pentadecyl)-[3,3']bibenzofuranylidene-2,2'-dione of formula (LIIIa) are obtained.

melting point: 542–549 K;

$^1$H-NMR (CDCl$_3$, 300 MHz), δ [ppm]: 0.8–1.8 m/32H; 3.03 m/1H; 7.39 d/1H; 9.03 d/1H,J=1.9 Hz.

EXAMPLE 9

Dehydration to isoxindigo; in toluene with thionyl chloride/N,N'-dimethylformamide and triethylamine 7.9 g of 3-hydroxy-5,7-bis(1-methyl-1-phenyl-ethyl)-3H-benzofuran-2-one (U.S. Pat. No. 5,614,572, column 34, compound N° 110) are placed in 25 ml of toluene with 2 ml of thionyl chloride and 3 drops of DMF and the reaction mixture is then slowly heated to 373 K at such a rate that the evolution of HCl and SO$_2$ remains vigorous yet controllable. The reaction mixture is then stirred at that temperature for a further hour. Approximately 25 ml of liquid are then distilled off in order to remove the excess thionyl chloride. The residue is diluted with 30 ml of toluene, then, at room temperature, 2.8 ml of triethylamine are added dropwise thereto. The thick, red reaction mixture is then heated under reflux for 30 min. After cooling to room temperature, the triethylamine hydrochloride which has precipitated is filtered off and the filtrate is concentrated to an oily consistency using a rotary evaporator. The isoxindigo is isolated from the residue, in the form of fine red crystals, by chromatography on silica gel (toluene/hexane 1:1 to 3:1) and trituration with benzine. 3.78 g (51% of the theoretical yield) of 5,7,5',7'-tetrakis(1-methyl-1-phenyl-ethyl)-[3,3']bibenzofuranylidene-2,2'-dione of formula (LVa) are obtained.

melting point: 468–471 K;

MS (DE-EI): m/e=536 (M$^+$, C$_{52}$H$_{48}$O$_4$).

EXAMPLE 10a 5,7-Di-tert-butyl-3-oxo-benzofuranone 3.8 g (0.0146 mol) of 5,7-di-tert-butyl-3-hydroxy-benzofuranone, 6.1 g (0.032 mol) of p-toluenesulfonic acid and 6.9 g (0.032 mol) of 4-acetamino-tetramethylpiperidine (TEMPO) are stirred in 100 ml of dichloromethane at room temperature for 24 hours. The yellow solution is then washed three times with 200 ml of 5% hydrochloric acid each time, dried over magnesium sulfate and concentrated to dryness by evaporation. Crystallisation of the residue from hexane yields 1 g of the above-mentioned compound.

melting point: 438–441 K.

EXAMPLE 10b

Dehydration to isoxindigo; with p-toluenesulfonic acid in 10 ml of acetic acid 0.5 g (0.0023 mol) of 7-tert-butyl-5-methoxy-benzofuranone (H.-D. Becker, K. Gustafsson., J. Org. Chem. 42, 2966, 1977), 0.6 g (0.0023 mol) of 5,7-di-tert-butyl-3-oxo-benzofuranone (Example 10a) and 0.2 g of p-toluenesulfonic acid are boiled under reflux in 10 ml of acetic acid for 16 hours. 20 ml of water are then added and the mixture is extracted three times with 30 ml of toluene each time. The extracts are washed with water and concentrated to dryness by evaporation. Addition of 10 ml of methanol and filtration yield 0.55 g of the isoxindigo (LXa).

melting point: 418–426 K.

EXAMPLE 11

Preparation of the isoxindigo (LVIa)

23.6 g of 3-(2-tert-butyl-4-hydroxy-phenyl)-propionic acid methyl ester (US 423070-A2), 10.1 g of glyoxylic acid monohydrate and 0.08 g of p-toluenesulfonic acid are boiled in 80 ml of 1,2-dichloroethane for 7 hours using a water separator. The reaction solution is then cooled, washed three times with 50 ml of water each time and freed of solvent using a rotary evaporator. 29.2 g of 3-(7-tert-butyl-3-hydroxy-2-oxo-2,3-dihydro-benzofuran-5-yl)-propionic acid methyl ester are obtained in the form of a yellowish oil. That yellowish oil is placed in 50 ml of toluene with 15 ml of thionyl chloride and 3 drops of DMF and the reaction mixture is then slowly heated to 100° C. at such a rate that the evolution of HCl and SO$_2$ remains vigorous yet controllable. The reaction mixture is then stirred at that temperature for a further hour. Approximately 50 ml of liquid are then distilled off in order to remove the excess thionyl chloride. The residue is diluted with 160 ml of toluene and, at room temperature, 14 ml of triethylamine are added dropwise thereto. The thick, red reaction mixture is then heated under reflux for 30 min. After cooling to room temperature, the triethylamine hydrochloride which has precipitated is filtered off and the filtrate is concentrated to an oily consistency using a rotary evaporator. The isoxindigo is crystallised out by adding 100 ml of acetonitrile, is filtered off, washed with acetonitrile and dried. 7.4 g (27% of the theoretical yield) of 3-[7,7'-di-tert-butyl-2,2'-dioxo-[3,3'] bibenzofuranyliden-5-yl]-5,5'-propionic acid methyl ester (LVIa) are obtained.

melting point: 497–499 K;

$^1$H-NMR (CDCl$_3$, 300 MHz), δ [ppm]: 1.43 s/9H; 2.69 t/2H; 3.01 t/2H; 3.70 s/3H; 7.30 d/1H; 8.77 d/1H,J=1.8 Hz.

EXAMPLE 12

Bis(5-cyclo-hexylidene)-7-tert-butyl-3-oxo-benzofuranone 5.1 g (0.01 mol) of bis(5-cyclo-hexylidene)-7-tert-butyl-3-hydroxy-benzofuranone (U.S. Pat. No. 5,614,572, compound 107, Table 1), 8.75 g (0.046 mol) of p-toluenesulfonic acid and 9.8 g (0.046 mol) of 4-acetamino-tetramethylpiperidine (TEMPO) are stirred in 60 ml of dichloromethane at room temperature for 48 hours. The yellow solution is then washed with 50 ml of 5% hydrochloric acid and 4×50 ml of water, dried over magnesium sulfate and concentrated to dryness by evaporation. The residue is dissolved in 100 ml of toluene, and the solution is heated under reflux for 1 hour and then concentrated by evaporation again, yielding 5 g of the above-mentioned compound.

EXAMPLE 12a

Bis-isoxindigo (LXIa)

22.0 g (0.1 mol) of 5-methoxy-7-tert-butyl-benzofuranone (prepared analogously to H.-D. Becker, K. Gustafsson.: J. Org. Chem. 42, 2966 (1977)), 27.5 g (0.05 mol) of bis(5-cyclohexylidene)-7-tert-butyl-3-oxo-benzofuranone (Example 12) and 1 g of p-toluenesulfonic acid are boiled under reflux in 130 ml of acetic acid for 22 hours. After cooling to room temperature, the resulting precipitate is recrystallised from dichloromethane/methanol and yields 9.2 g of bis-isoxindigo (LXIa).

melting point: 532–537 K.

EXAMPLE 13

Bis-isoxindigo (LXIIa)

4.9 g (0.02 mol) of 5,7-di-tert-butyl-benzofuranone (H.-D. Becker, K. Gustafsson.: J. Org. Chem. 42, 2966 (1977)), 4.9 g (0.01 mol) of bis(5-cyclohexylidene)-7-tert-butyl-3-oxo-benzofuranone (Example 12) and 0.3 g of p-toluenesulfonic acid are boiled under reflux in 25 ml of acetic acid for 10 hours. 125 ml of water are then added and the resulting precipitate is filtered off with suction and chromatographed on silica gel (hexane/toluene 2:1). Crystallisation of the pure fractions from methanol yields 1.25 g of bis-isoxindigo (LXIIa).

melting point: 577–581 K.

EXAMPLE 14

Isoxindigo (LIVa)

300 ml of toluene, 30 g (0.117 mol) of 2,4-dicyclohexylphenol (synthesis, for example, according to: Kozlikovskii, Ya. et al.: Zh. Org. Khim. (1984), 20(1), 121–4), 121.9 ml of 50% aqueous glyoxylic acid and 0.5 g of p-toluenesulfonic acid monohydrate are added in succession, with stirring, to a 1.5 litre multi-necked vessel equipped with stirrer, dropping funnel, water separator, condenser and thermometer. The reaction mixture is then refluxed vigorously while stirring well, during which the water present in the glyoxylic acid and the water of reaction of the first step separates. After a reflux time of approximately 3 hours, the separation of water ceases, leaving a homogeneous, slightly yellow solution of the hydroxybenzofuranone. The reaction mixture is then diluted with 40 ml of a linear $C_9$–$C_{13}$alkylbenzene that boils at 548–585 K. (®Marlican, Hüls). Then, under normal pressure and at a heating-bath temperature of up to 315 K, approximately 200 ml of toluene are distilled off. At the end of the distillation, the internal temperature is approximately 394 K. The light-yellow, oily mixture is cooled to an internal temperature of approximately 333 K and 13.9 ml of triethylamine are added thereto. 79.8 ml of thionyl chloride are then added dropwise from the dropping funnel sufficiently rapidly that the evolution of HCl and $SO_2$ remains vigorous yet controllable. The addition lasts approximately 75 min, and the internal temperature is 333–337 K. When the formation of gas has virtually subsided, the reaction mixture is stirred for a further hour at 373 K. The heating control of the heating bath is then increased to 573 K. The temperature of the reaction mixture rises to 495 K over a period of approximately 35 min, during which a further 105 ml of toluene distil off. At the same time, a vigorous stream of HCl gas escapes once more. If the evolution of gas is too violent, the heating rate is reduced accordingly. The mixture, which is already deep-red, is then stirred for a further 2 hours at 453–463 K. The thick, dark-red to black crystal suspension is cooled to approximately 422 K; 200 ml of n-butanol followed by 400 ml of ethanol are then added through the condenser. The crystal suspension is stirred under reflux for approximately a further hour, is then cooled to 273–278 K and filtered off. The crystal cake is washed with sufficient cold ethanol (approximately 600 ml) until the filtrate is clearly no longer brown-tinged but is faintly red in colour. The crystalline dye is then dried at 80° C./50 mbar, yielding 13.5 g (39% of the theoretical yield based on 2,3-dicyclohexylphenol) of fine, deep-red, shiny crystals of 5,7,5',7'-tetra-cyclohexyl-[3,3'] bibenzofuranylidene-2,2'-dione of formula (LIVa).

| melting point: | 517–524 K. | | |
| elemental analysis: | | % C | % H |
| | calc. | 81.04 | 8.16 |
| | found | 80.92 | 8.23 |

EXAMPLE 15

Process for the Dreparation of dibenzonalhthyrones (L) to (LXII)

0.02 mol of isoxindigo is boiled under reflux in 100 ml of n-butanol[1] and 50 ml of pyridine for a sufficiently long period (normally 10–40 hours) until the red colour of the isoxindigo has completely changed to the yellow colour of the dibenzonaphthyrone. The mixture is then cooled in an ice-bath, and the resulting crystals are filtered off with suction, washed with methanol and dried.

[1] In the case of compound LVI, Table 1, methanol is used in order to avoid transesterification.

TABLE 1

The dibenzophthyrones (L) to (LXII) listed in Table 1 are prepared analogously to Example 15.

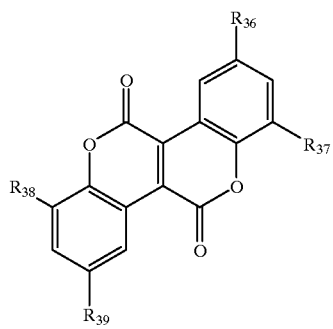

| isoxindigo | dibenzonaphthyrone | reaction time (hours) | m.p. (K.) | analysis |
|---|---|---|---|---|
| (La) Example 3 a, b, c | (L), wherein $R_{36}$, $R_{39}$ are methyl, and $R_{37}$, $R_{38}$ are tert-butyl | 20 | 556–560 | C: calc./found 77.20/77.24 H: calc./found 6.98/6.86 yield: 87% of the theoretical yield |
| (LIa) Example 1, 2 a, b, c | (LI), wherein $R_{36}$, $R_{39}$, $R_{37}$, $R_{38}$ are tert-butyl | 16 | 518–520 | $^1$H-NMR (CDCl$_3$), 300 MHz, δppm: 1.42 s (t-Bu), 1, s (t-Bu), 7.67 d (ArH), 9.25 d (ArH); J = 2.4 Hz. yield: 95% of the theoretical yield |
| (LIIa) Example 4 | (LII), wherein $R_{36}$, $R_{39}$ are methyl, and $R_{37}$, $R_{38}$ are 1,1',3,3'-tetramethyl-butyl | 25 | 533–537 | C: calc./found 79.03/79.14 H: calc./found 8.58/8.65 yield: 70% of the theoretical yield |
| (LIIIa) Example 8 | (LIII), wherein $R_{36}$, $R_{39}$ are tert-butyl, and $R_{37}$, $R_{38}$ are 1-methylpentadecyl | 16 | 347–354 | C: calc./found 81.50/81.31 H: calc./found 10.75/10.51 yield: 67% of the theoretical yield |
| (LIVa) Example 14 | (LIV), wherein $R_{36}$, $R_{39}$, $R_{37}$, $R_{38}$ are cyclohexyl | 27 | 547–553 | C: calc./found 81.04/80.98 H: calc./found 8.16/8.21 yield: 73% of the theoretical yield |
| (LVa) Example 9 | (LV), wherein $R_{36}$, $R_{39}$, $R_{37}$, $R_{38}$ are 1-methyl-1'-phenyl-ethyl | 18 | 512–516 | C: calc./found 84.75/84.76 H: calc./found 6.56/6.49 yield: 98% of the theoretical yield |
| (LVIa) Example 11 | (LVI), wherein $R_{36}$, $R_{39}$ are propionic acid methyl ester and $R_{37}$, $R_{38}$ are tert-butyl | 42 | 523–527 | C: calc./found 70.06/69.98 H: calc./found 6.61/6.55 yield: 93% of the theoretical yield |
| (LVIIa) Example 6 | (LVII), wherein $R_{36}$, $R_{39}$ are chlorine, and $R_{37}$, $R_{38}$ are tert-butyl | 25 | 658 | C: calc./found 64.73/64.68 H: calc./found 4.98/4.73 yield: 63% of the theoretical yield |
| (LVIIIa) Example 7 | (LVIII), wherein $R_{36}$, $R_{39}$ are thiophenyl, and $R_{37}$, $R_{38}$ are tert-butyl | 26 | 517–522 | C: calc./found 72.95/73.09 H: calc./found 5.44/5.49 yield: 94% of the theoretical yield |
| (LIXa) Example 5 | (LIX), wherein $R_{36}$, $R_{39}$ are methoxy, and $R_{37}$, $R_{38}$ are tert-butyl | 16 | 582–584 | C: calc./found 71.54/71.53 H: calc./found 6.47/6.55 yield: 95% of the theoretical yield |
| (LXa) Example 10b | (LX), wherein $R_{36}$ is methoxy, and $R_{37}$, $R_{38}$, $R_{39}$ are tert-butyl | 17 | 478–480 | $^1$H-NMR (CDCl$_3$), 300 MHz, δppm: 1.42 s (t-Bu), 1.54 s (t-Bu), 1.57 s (t-Bu), 3.93 s (OMe) 7.23 d (ArH), 7.80 d (ArH), 8.75 d (ArH), 9.25 d (ArH), J = 2.2 Hz. |
| (LXIa) Example | (LXI) | 25 | 521–526 | C: calc./found 75.31/75.21 |

| | | | | H: calc./found |
|---|---|---|---|---|
| | | | | 6.77/6.86 |
| | | | | yield: 85% of the theoretical yield |

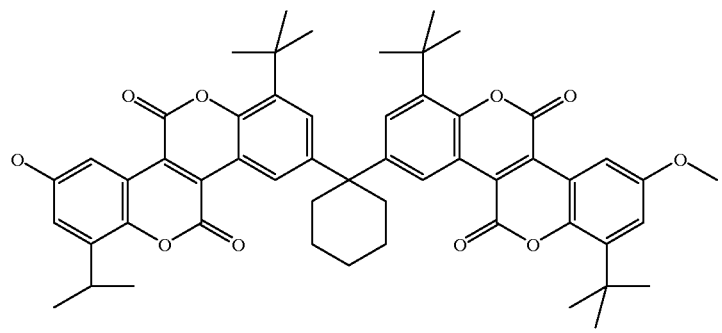

| (LXIIa) | (LXI) | | 7 | 655 | C: calc./found |
|---|---|---|---|---|---|
| Example 13 | | | | | 78.78/78.68 |
| | | | | | H: calc./found |
| | | | | | 7.68/7.57 |
| | | | | | yield: 92% of the theoretical yield |

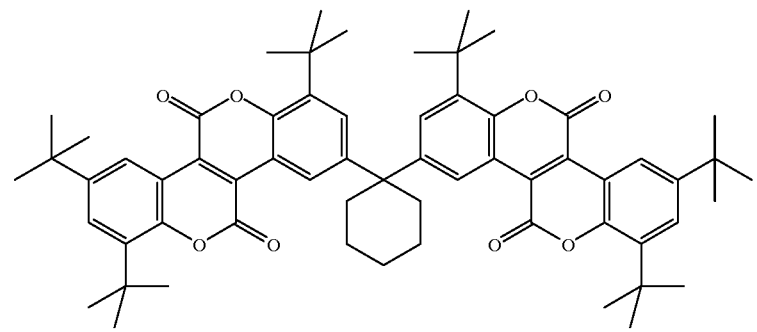

EXAMPLE 16

Production of Injection-moulded Plates

Dibenzonaphthyrone of formulae (L) to (LXII) and 1500 g of plastics material that has been pre-dried at 473–543 K are briefly mixed by hand and then mixed for 5 min at 50 rev/min in a tumbler mixer. The mixture is then pre-extruded at 543 K in a 25 mm 1-screw extruder (Collin). The compound is then processed on a microprocessor-controlled injection-moulding machine (™Ferromatik FM 40, Kl öckner). The residence time of the polymer (dependent on the cycle time, screw volume and plastification volume) is 5 min, during which the back pressure and the screw speed are kept low. That promotes homogeneous processing of the plastics material and prevents the generation of heat due to friction. The first injection-mouldings (platelets measuring 65×25×1.5 mm) are discarded. The injection-mouldings produced at temperatures of from 473 K to 573 K in a residence time of 5 minutes are distinguished by excellent colour fastness properties, such as very high heat-stability, high light-fastness, good migration-stability and high colour intensity. The colour fastness properties are compared visually with a standard or are determined colorimetrically.

EXAMPLE 16a

Production of injection-moulded plates using polyethylene terephthalate (PET) (™MELINAR PURA, ICI)

0.1 g of dibenzonaphthyrone of formulae (L) to (LXII) is mixed with polyethylene terephthalate (PET) (™MELINAR PURA, ICI) in accordance with the above Example 16 and processed to form injection-mouldings. The injection-mouldings are produced at 543 K, 553 K, 563 K and 573 K in 2 minutes in each case. They are distinguished by very high heat-stability, high light-fastness, good migration-stability and high colour intensity.

EXAMPLE 16b

Production of injection-moulded plates using polybutylene terephthalate (PBTB)(™CRATIN S 600, CIBA)

0.1 g of dibenzonaphthyrone of formulae (L) to (LXII) is mixed with polybutylene terephthalate (PBTB) (™CRATIN S 600, CIBA) in accordance with the above Example 16 and processed to form injection-mouldings. The injection-mouldings are produced at 533 K, 548 K and 563 K in 5 minutes in each case. They have very high heat-stability, high light-fastness, good migration-stability and high colour intensity.

What is claimed is:
1. A dibenzonaphthyrone of formula (I)
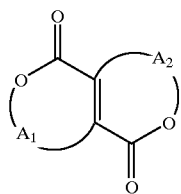
(I)
wherein $A_1$ and $A_2$ are each independently of the other unsubstituted or mono- to tetra-substituted o-$C_6$–$C_{18}$arylene, with the proviso that formula (I) does not represent a dibenzonaphthyrone of the formula
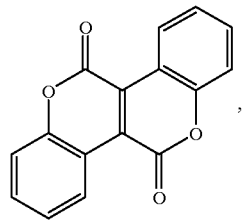
II
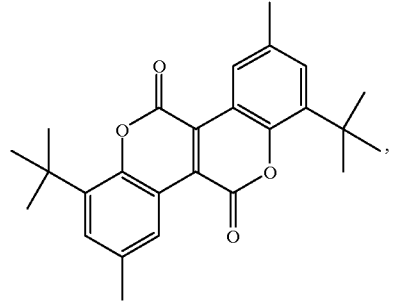
III
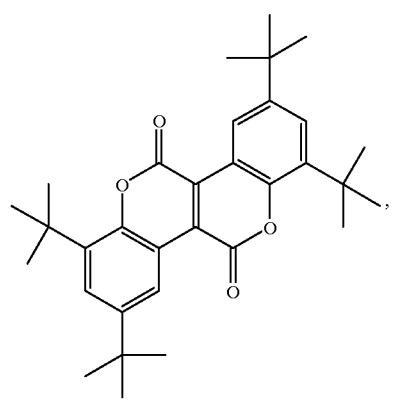
IV
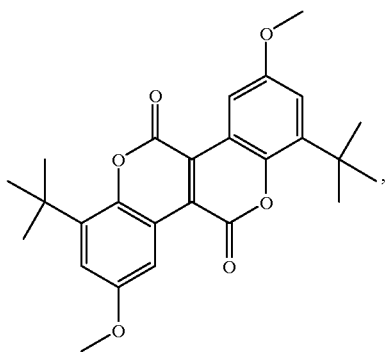
V
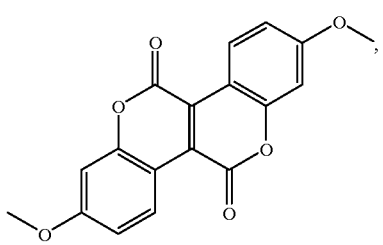
VI
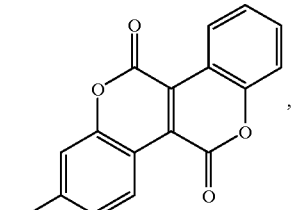
VII
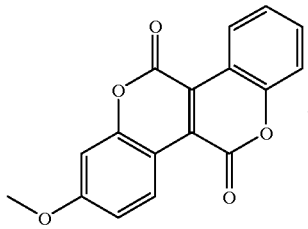
VIII
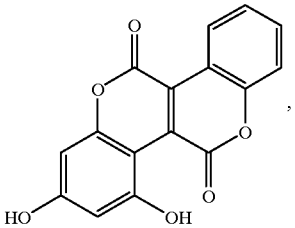
IX
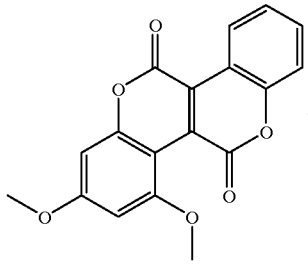
X

XI
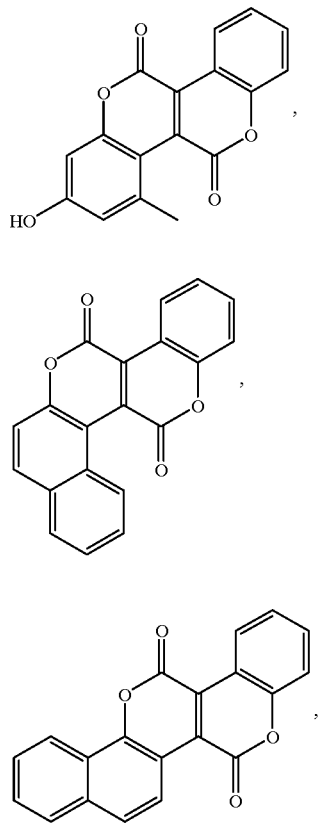
XII
XIII
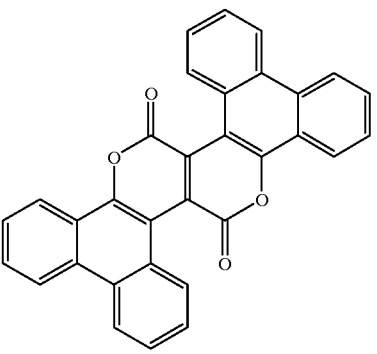
XIV
or
XV
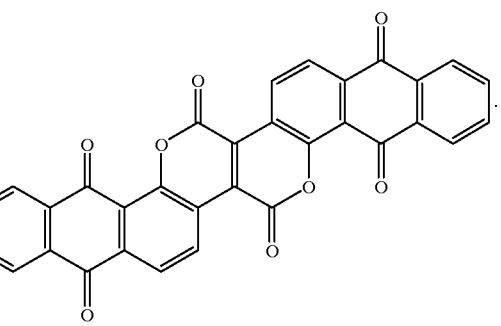
2. A dibenzonaphthyrone according to claim 1 of the formula
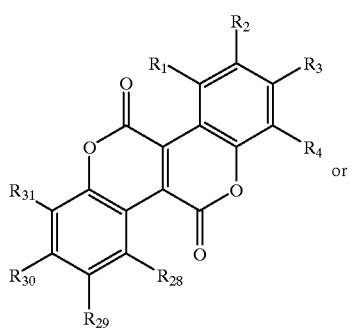
(XVIa)
or
a bis-dibenzonaphthyrone of the formula (XVIb)

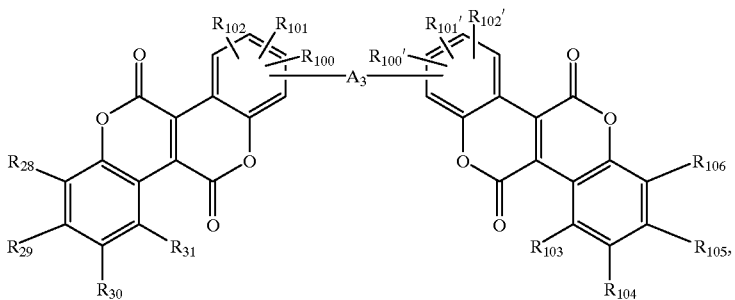

wherein $A_3$ is a single bond, or $C_1$–$C_{24}$alkylene unsubstituted or mono- or poly-substituted by halogen, hydroxy, oxo, cyano, $OCOR_6$, $COOR_6$, $COO^-X^+$, $SO_3^-X^+$ or by $SO_3R_6$, a polycyclic radical or $C_5$–$C_{12}$cycloalkylene, each of which may be uninterrupted or interrupted one or more times by O, N, P, S or by $NR_6$, and $C_6$–$C_{24}$arylen and $A_1$–$A_{24}$heteroarylen, and $R_{100}$, $R_{101}$, $R_{102}$ and $R_{100'}$, $R_{101'}$, $R_{102'}$ and $R_{103}$, $R_{104}$, $R_{105}$, $R_{106}$ have independently of one another the same meanings as $R_1$, and $R_1$, $R_2$, $R_3$, $R_4$ and $R_{28}$, $R_{29}$, $R_{30}$ or $R_{31}$ are each independently of others cyano, $NO_2$, $R_5$, $NR_5R_6$, $NR_7COR_5$, $NR_7COOR_5$, $N=CR_5R_6$, $CONR_7R_8$, $OR_5$, $COOR_5$, $COO^-X^+$, $SR_5$, $SOR_5$, $SO_2R_5$, $SO_2NR_7R_8$, $SO_3R_5$ or $SO_3^-X^+$, it being possible, where applicable, for the pairs of radicals $R_1$ and $R_2$, $R_2$ and $R_3$, $R_3$ and $R_4$ or $R_5$ and $R_6$, and also $R_{28}$ and $R_{29}$, $R_{29}$ and $R_{30}$ or $R_{30}$ and $R_{31}$ to be, in addition, joined together by a direct bond so that a 5- or 6-membered ring is produced;

$R_5$ is hydrogen, or $C_1$–$C_{25}$alkyl, $C_5$–$C_{12}$-cycloalkyl or $C_2$–$C_{24}$alkenyl each of which is unsubstituted or mono- or poly-substituted by halogen, hydroxy, oxo, cyano, $OCOR_6$, $COOR_6$ or by $COO^-X^+$ and each of which may be uninterrupted or interrupted one or more times by O, S or by $NR_6$, or is $C_6$–$C_{18}$aryl, $C_7$–$C_{18}$aralkyl or $A_5$–$A_{18}$heteroaryl each of which is unsubstituted or mono- or poly-substituted by halogen, nitro, cyano, $OR_6$, $SR_6$, $NR_7R_8$, $CONR_7R_8$, $OCOR_6$, $COOR_6$, $COO^-X^+$, $SO_2R_6$, $SO_2NR_7R_8$, $SO_3R_6$, $SO_3^-X^+$, $NR_7COR_6$ or by $NR_7COOR_6$, $R_6$ is hydrogen, or $C_1$–$C_{25}$alkyl unsubstituted or mono- or poly-substituted by halogen, hydroxy, oxo or by cyano, or $OCO—R_{10}$, $COO—R_{10}$ or $COO^-X^+$, or $C_2$–$C_{24}$alkenyl, each of which may be uninterrupted or interrupted one or more times by O, S or $NR_7$, or is $C_6$–$C_{18}$aryl, $C_7$–$C_{18}$aralkyl or $A_5$–$A_{18}$heteroaryl each of which is unsubstituted or mono- or poly-substituted by halogen, nitro, cyano, hydroxy, $OR_7$, $SR_7$, $NR_7R_8$, $CONR_7R_8$, $COOR_7$, $OCOR_7$, $COOH$ or by $COO^-X^+$, $R_7$ and $R_8$ independently of each other are hydrogen, $C_6$–$C_{18}$aryl, $C_7$–$C_{18}$aralkyl, or are $C_1$–$C_{25}$alkyl or $C_2$–$C_{24}$alkenyl each unsubstituted or mono- or poly-substituted by halogen, hydroxy, $C_1$–$C_{12}$alkoxy, $OCO—R_{10}$, $COO—R_{10}$ or by $COO^-X^+$, or $R_7$ and $R_8$ together with the common N are pyrrolidine, piperidine, piperazine or morpholine each unsubstituted or mono- to tetra-subsfituted by $C_1$–$C_4$alkyl, or are carbazole, phenoxazine or phenothiazine, $X^+$ is a cation $Li^+$, $Na^+$, $K^+$, $Mg^{++}_{1/2}$, $Ca^{++}_{1/2}$, $Sr^{++}_{1/2}$, $Ba^{++}_{1/2}$, $Cu^+$, $Cu^{++}_{1/2}$, $Zn^{++}_{1/2}$, $Al^{+++}_{1/3}$ or $[NR_7R_8R_{10}R_{11}]^+$, and $R_{10}$ and $R_{11}$ independently of each other are hydrogen, $C_1$–$C_{25}$alkyl, $C_6$–$C_{18}$aryl or $C_7$–$C_{18}$aralkyl, with the proviso that, in formula (XVIa), dibenzonaphthyrones of formulae (II) to (XV) are excluded.

3. A dibenzonaphthyrone according to claim 1 of the formula (XVII)

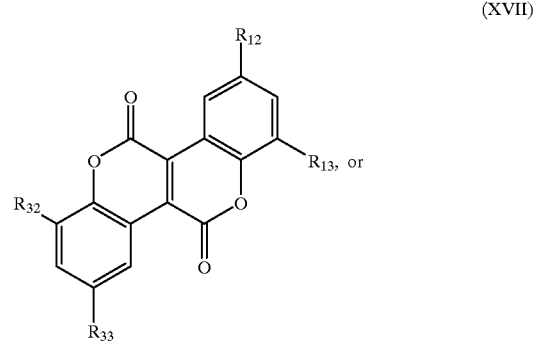

a bis-dibenzonaphthyrone of the formula (XVIII)

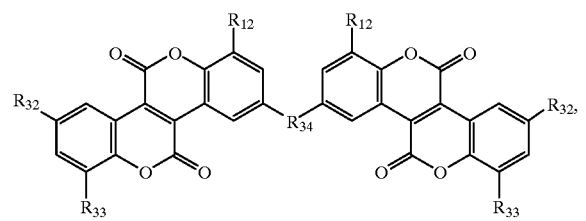

wherein $R_{12}$, $R_{13}$, $R_{32}$ and $R_{33}$ independently of one another are hydrogen, halogen, $NO_2$, $R_{14}$, $OR_{14}$, $SR_{14}$, and $R_{34}$ is a single bond, $C_1$–$C_{24}$alkylene or $C_5$–$C_{12}$cycloalkylene, wherein $R_{14}$ is $C_1$–$C_{25}$alkyl which is unsubstituted or mono- or poly-substituted by oxo, cyano, $COOR_{16}$, $OCOR_{16}$ or by $COO^-X1^+$ and which may be uninterrupted or interrupted one or more times by O, or $C_6$–$C_{10}$aryl or $C_7$–$C_{10}$aralkyl each unsubstituted or mono- or poly-substituted by halogen, nitro, cyano, $OR_{16}$, $NR_{16}R_{17}$, $CONR_{16}R_{17}$, $COOR_{16}$, $OCOR_{16}$, $NR_{18}COR_{16}$ or by $NR_{18}COOR_{16}$;

$X1^+$ is a cation $Na^+$, $K^+$, $Mg^{++}{}_{1/2}$, $Ca^{++}{}_{1/2}$, $Zn^{++}{}_{1/2}$, $Al^{+++}{}_{1/3}$ or $[NR_{16}R_{17}R_{18}R_{19}]^+$; and $R_{16}$ and $R_{17}$ independently of each other are hydrogen, $C_6$–$C_{10}$aryl, $C_7$–$C_{10}$aralkyl, or $C_1$–$C_8$alkyl which is unsubstituted or mono- or poly-substituted by halogen, hydroxy or by $C_1$–$C_4$alkoxy; or $R_{16}$ and $R_{17}$ together with the common N are pyrrolidine, piperidine, piperazine or morpholine each unsubstituted or mono- to tetra-substituted by $C_1$–$C_4$alkyl; and $R_{18}$ and $R_{19}$ independently of each other are hydrogen, $C_1$–$C_{12}$alkyl, $C_6$–$C_{10}$aryl or $C_7$–$C_{10}$aralkyl.

* * * * *